US006994827B2

(12) United States Patent
Safir et al.

(10) Patent No.: US 6,994,827 B2
(45) Date of Patent: Feb. 7, 2006

(54) PARALLEL SEMICONTINUOUS OR CONTINUOUS REACTORS

(75) Inventors: Adam Safir, Berkeley, CA (US); Ralph Nielsen, San Jose, CA (US); Thomas H. McWaid, Fremont, CA (US); Richard Tiede, San Jose, CA (US); Lynn Van Erden, Livermore, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 614 days.

(21) Appl. No.: 09/873,176

(22) Filed: Jun. 1, 2001

(65) Prior Publication Data

US 2003/0156989 A1 Aug. 21, 2003

Related U.S. Application Data

(60) Provisional application No. 60/255,716, filed on Dec. 14, 2000, and provisional application No. 60/209,142, filed on Jun. 3, 2000.

(51) Int. Cl.
| | |
|---|---|
| *G01N 33/00* | (2006.01) |
| *B01N 3/02* | (2006.01) |
| *B01N 3/00* | (2006.01) |
| *B01J 10/00* | (2006.01) |
| *B32B 27/04* | (2006.01) |

(52) U.S. Cl. ............... 422/100; 422/102; 422/129; 422/131; 422/135; 422/81; 366/198; 366/172.1; 222/252

(58) Field of Classification Search ............... 422/135, 422/99–104, 129–131, 81; 73/866; 366/198, 366/172.1; 222/252
See application file for complete search history.

(56) References Cited

U.S. PATENT DOCUMENTS

| | | | |
|---|---|---|---|
| 94,830 | A | 9/1869 | King |
| 1,111,374 | A | 9/1914 | Goddard et al. |
| 1,281,610 | A | 10/1918 | Lundahl |
| 1,841,434 | A | 1/1932 | Gibson |

(Continued)

FOREIGN PATENT DOCUMENTS

| | | |
|---|---|---|
| CA | 266759 | 6/1990 |
| EP | 529 504 A2 | 3/1993 |
| EP | 635 713 A1 | 1/1995 |
| EP | 783 922 A1 | 7/1997 |

(Continued)

OTHER PUBLICATIONS

Nelles, et al., *For Development of Test Reactors for Heterogenic Solid–Liquid–Processes*, Chem. Tech. 1975, pp. 714–716, vol. 27.

(Continued)

*Primary Examiner*—Jill Warden
*Assistant Examiner*—Brian R. Gordon
(74) *Attorney, Agent, or Firm*—Senniger Powers

(57) ABSTRACT

Parallel semi-continuous or continuous reactors are disclosed. The parallel reactors preferably comprise four or more reaction vessels. The reaction vessels are preferably small volume reaction vessels, preferably pressure reaction vessels, and/or preferably integral with a common reactor block. The reaction vessels can comprise shaft-driven stirrers. At least two, preferably at least three or at least four liquid feed lines can provide selective fluid communication between each of the reaction vessels and one or more liquid reagent sources. Additional features, suitable in connection with parallel reactors or with single reaction vessels are also disclosed.

67 Claims, 18 Drawing Sheets

U.S. PATENT DOCUMENTS

| | | | |
|---|---|---|---|
| 2,025,379 A | 12/1935 | Croasdale, Jr. | |
| 2,202,860 A | 6/1940 | McPhee et al. | |
| 2,484,391 A | 10/1949 | Treiss, Jr. | |
| 2,637,537 A | 5/1953 | Ernst | |
| 2,766,022 A | 10/1956 | Bender | |
| 2,991,161 A | 7/1961 | Gasche | |
| 2,996,363 A | 8/1961 | Ruyak | |
| 3,143,167 A | 8/1964 | Vieth | |
| 3,319,940 A | 5/1967 | Mentnech | |
| 3,326,610 A | 6/1967 | Baermann et al. | |
| 3,455,540 A | 7/1969 | Marcmann | |
| 3,456,923 A | 7/1969 | Zeuzem | |
| 3,603,564 A | 9/1971 | Price et al. | |
| 3,622,968 A | 11/1971 | Silverman | |
| 3,676,653 A | 7/1972 | Arens et al. | |
| 3,680,843 A | 8/1972 | Lu et al. | |
| 3,693,941 A | 9/1972 | Suchy | |
| 3,697,053 A | 10/1972 | Will | |
| 3,718,032 A | 2/1973 | Gray | |
| 3,778,757 A | 12/1973 | Houston | |
| 3,909,647 A | 9/1975 | Peterson | |
| 4,037,826 A | 7/1977 | Hulslander et al. | |
| 4,065,107 A | 12/1977 | Van Horbek | |
| 4,099,923 A | 7/1978 | Milberger | |
| 4,106,825 A | 8/1978 | Ruyak | |
| 4,151,400 A | 4/1979 | Smith et al. | |
| 4,175,875 A | 11/1979 | Van Horbek | |
| 4,195,131 A | 3/1980 | Papas | |
| 4,199,265 A | 4/1980 | Sanderson et al. | |
| 4,229,110 A | 10/1980 | Lücke | |
| 4,235,592 A | 11/1980 | Smith et al. | |
| 4,243,636 A | 1/1981 | Shiraki et al. | |
| 4,325,914 A | 4/1982 | Ruyak | |
| 4,355,906 A | 10/1982 | Ono | |
| 4,370,662 A | 1/1983 | Hou et al. | |
| 4,391,338 A | 7/1983 | Patashnick et al. | |
| 4,438,074 A | 3/1984 | Wilt | |
| 4,461,743 A * | 7/1984 | Chowdhury et al. | 422/129 |
| 4,469,445 A | 9/1984 | Wurtz | |
| 4,506,982 A | 3/1985 | Smithers et al. | |
| 4,517,338 A | 5/1985 | Urdea et al. | |
| 4,568,195 A | 2/1986 | Herz et al. | |
| 4,594,228 A | 6/1986 | Lambert, Jr. et al. | |
| 4,598,049 A | 7/1986 | Zelinka et al. | |
| 4,640,023 A | 2/1987 | Mori et al. | |
| 4,671,941 A | 6/1987 | Niina et al. | |
| 4,675,026 A | 6/1987 | Riemer et al. | 44/280 |
| 4,721,874 A | 1/1988 | Emmert | |
| 4,741,200 A | 5/1988 | Hammerle | |
| 4,746,490 A | 5/1988 | Saneii | |
| 4,748,002 A | 5/1988 | Neimark et al. | |
| 4,779,451 A | 10/1988 | Ezawa et al. | |
| 4,799,862 A | 1/1989 | Davidson et al. | |
| 4,810,099 A | 3/1989 | Langsetmo et al. | |
| 4,858,637 A | 8/1989 | Rempel et al. | |
| 4,865,986 A | 9/1989 | Coy et al. | |
| 4,901,221 A | 2/1990 | Kodosky et al. | |
| 4,910,523 A | 3/1990 | Huguenin et al. | |
| 4,924,444 A | 5/1990 | Castellanos | |
| 4,944,923 A | 7/1990 | Heinrichs et al. | |
| 4,983,046 A | 1/1991 | Murata et al. | |
| 5,061,630 A | 10/1991 | Knopf et al. | |
| 5,074,671 A | 12/1991 | Roueche et al. | |
| 5,098,669 A | 3/1992 | Kawanami et al. | |
| 5,117,550 A | 6/1992 | Nadeau et al. | |
| 5,143,854 A | 9/1992 | Pirrung et al. | |
| 5,145,255 A | 9/1992 | Shimada et al. | |
| 5,152,488 A | 10/1992 | Richardson | 248/274 |
| 5,154,891 A | 10/1992 | Brenner | |
| 5,191,791 A | 3/1993 | Gerardi et al. | |
| 5,201,215 A | 4/1993 | Granstaff et al. | |
| 5,217,695 A | 6/1993 | Augustine et al. | |
| 5,224,174 A | 6/1993 | Schneider et al. | |
| RE34,386 E | 9/1993 | Davidson et al. | |
| 5,252,296 A | 10/1993 | Zuckermann et al. | |
| 5,282,543 A * | 2/1994 | Picozza et al. | 220/255 |
| 5,291,587 A | 3/1994 | Kodosky et al. | |
| 5,297,867 A | 3/1994 | Holman | |
| 5,304,355 A | 4/1994 | Yant et al. | |
| 5,316,728 A | 5/1994 | Hayashi et al. | |
| 5,324,483 A | 6/1994 | Cody et al. | |
| 5,356,756 A | 10/1994 | Cavicchi et al. | |
| 5,357,964 A | 10/1994 | Spivey et al. | |
| 5,367,879 A | 11/1994 | Doke et al. | |
| 5,375,470 A | 12/1994 | Matsushima et al. | |
| 5,380,485 A | 1/1995 | Takahashi et al. | |
| 5,380,495 A | 1/1995 | Chang et al. | |
| 5,395,594 A | 3/1995 | Nokihara et al. | |
| 5,399,014 A | 3/1995 | Takata et al. | |
| 5,407,270 A | 4/1995 | Barile et al. | |
| 5,437,838 A | 8/1995 | De Moranville et al. | |
| 5,439,236 A | 8/1995 | Musil | |
| 5,443,791 A | 8/1995 | Cathcart et al. | |
| 5,469,369 A | 11/1995 | Rose-Pehrsson et al. | |
| 5,472,278 A | 12/1995 | Kawaoka et al. | |
| 5,499,193 A | 3/1996 | Sugawara et al. | |
| 5,503,805 A | 4/1996 | Sugarman et al. | |
| 5,515,683 A | 5/1996 | Kessler | |
| 5,524,636 A | 6/1996 | Sarvazyan et al. | |
| 5,538,694 A | 7/1996 | Delius | |
| 5,541,314 A | 7/1996 | McGraw et al. | |
| 5,544,489 A | 8/1996 | Moren | |
| 5,546,301 A | 8/1996 | Agrawal et al. | |
| 5,576,946 A | 11/1996 | Bender et al. | |
| 5,593,642 A | 1/1997 | DeWitt et al. | |
| 5,593,839 A | 1/1997 | Hubbell et al. | |
| 5,601,141 A | 2/1997 | Gordon et al. | |
| 5,602,756 A | 2/1997 | Atwood et al. | |
| 5,609,826 A | 3/1997 | Cargill et al. | |
| 5,611,059 A | 3/1997 | Benton et al. | |
| 5,670,269 A | 9/1997 | Hamada et al. | |
| 5,698,163 A | 12/1997 | Mandel | |
| 5,714,127 A | 2/1998 | DeWitt et al. | |
| 5,716,584 A | 2/1998 | Baker et al. | |
| 5,732,277 A | 3/1998 | Kodosky et al. | |
| 5,734,098 A | 3/1998 | Kraus et al. | |
| 5,738,439 A | 4/1998 | Flower | |
| 5,746,982 A | 5/1998 | Saneii et al. | |
| 5,762,881 A | 6/1998 | Harness et al. | |
| 5,789,258 A | 8/1998 | Drinkwine et al. | |
| 5,792,431 A | 8/1998 | Moore et al. | |
| 5,796,016 A * | 8/1998 | Muller | 73/866 |
| 5,802,856 A | 9/1998 | Schaper et al. | |
| 5,812,394 A | 9/1998 | Lewis et al. | |
| 5,819,842 A | 10/1998 | Potter et al. | |
| 5,837,199 A | 11/1998 | Dumschat | |
| 5,841,959 A | 11/1998 | Guiremand | |
| 5,856,101 A | 1/1999 | Hubbell et al. | |
| 5,862,052 A | 1/1999 | Nixon et al. | |
| 5,866,342 A | 2/1999 | Antonenko et al. | |
| 5,869,643 A | 2/1999 | Chatelain et al. | |
| 5,871,278 A | 2/1999 | Harry et al. | |
| 5,879,637 A * | 3/1999 | Titmas | 422/129 |
| 5,888,830 A | 3/1999 | Mohan et al. | |
| 5,961,925 A | 10/1999 | Ruediger et al. | 422/99 |
| 5,985,356 A | 11/1999 | Schultz et al. | |
| 6,030,917 A | 2/2000 | Weinberg et al. | |
| 6,036,923 A | 3/2000 | Laugharn, Jr. et al. | |
| 6,060,024 A * | 5/2000 | Hutchins et al. | 422/81 |
| 6,063,633 A | 5/2000 | Willson, III | |
| 6,074,610 A * | 6/2000 | Huang et al. | 422/99 |

| | | | | |
|---|---|---|---|---|
| 6,083,763 | A | * | 7/2000 | Balch .................... 436/518 |
| 6,086,831 | A | | 7/2000 | Harness et al. |
| 6,109,780 | A | | 8/2000 | Lesniak |
| 6,132,686 | A | | 10/2000 | Gallup et al. |
| 6,159,368 | A | * | 12/2000 | Moring et al. ......... 210/321.75 |
| 6,190,619 | B1 | * | 2/2001 | Kilcoin et al. ............. 422/131 |
| 6,440,374 | B1 | * | 8/2002 | Jelinek et al. ............. 422/109 |
| 6,548,026 | B1 | * | 4/2003 | Dales et al. ............... 422/138 |
| 6,696,298 | B2 | * | 2/2004 | Cook et al. .................... 436/54 |
| 6,818,186 | B2 | * | 11/2004 | Burns et al. ................ 422/131 |
| 2003/0012700 | A1 | * | 1/2003 | Carnahan .................... 422/102 |
| 2003/0069411 | A1 | * | 4/2003 | Brennan .................... 536/25.3 |
| 2003/0072689 | A1 | * | 4/2003 | Cracauer et al. ............ 422/131 |
| 2004/0044170 | A1 | * | 3/2004 | DeBruin ..................... 528/272 |
| 2004/0126878 | A1 | * | 7/2004 | Ramos et al. ............... 435/366 |

FOREIGN PATENT DOCUMENTS

| | | |
|---|---|---|
| EP | 796 654 A2 | 9/1997 |
| EP | 0 916 397 A2 | 5/1999 |
| EP | 963 791 A2 | 12/1999 |
| FR | 1418757 | 10/1965 |
| FR | 2630927 | 11/1989 |
| GB | 989424 | 4/1965 |
| GB | 1408199 | 10/1975 |
| JP | 4-18424 | 1/1992 |
| JP | 10-182501 | 7/1998 |
| WO | WO 90/02605 | 3/1990 |
| WO | WO 93/20130 | 10/1993 |
| WO | WO 96/14930 | 5/1996 |
| WO | WO 97/09353 | 3/1997 |
| WO | WO 97/10896 | 3/1997 |
| WO | WO 98/07026 | 2/1998 |
| WO | WO 98/13137 | 4/1998 |
| WO | WO 98/15501 | 4/1998 |
| WO | WO 98/15813 | 4/1998 |
| WO | WO 98/20130 | 5/1998 |
| WO | WO 98/22212 | 5/1998 |
| WO | WO 98/36826 | 8/1998 |
| WO | WO 98/39099 | 9/1998 |
| WO | WO 98/40159 | 9/1998 |
| WO | WO 98/57740 | 12/1998 |
| WO | WO 99/30817 | 6/1999 |
| WO | WO 00/09255 | 2/2000 |
| WO | WO 01/36087 | 5/2001 |

OTHER PUBLICATIONS

Tietze, A., et al., "Temperature Oscillation Calorimetry in Stirred Tank Polymerization Reactors," *Dechema Monogr.* 1995, 131, 673–680.

Vignes, S., et al., *Comp. Rend. Congr. Indust.* 1961, 405–411.

World Wide Web brinkman.com, 1997 "Brinkmann Horizon Stirrers and Hotplace Stirrers" Information.

World Wide Web calbay.com, Mar. 31, 1998 "Viscoliner" information.

World Wide Web argotech.com/quest, May 18, 1998 "NAUTILUS 2400" information.

World Wide Web argotech.com/quest, May 18, 1998 "QUEST 210" information.

World Wide Web tecan.ch, Jul. 14, 1998 "CAVRO RSP 9000 Robotic Sample Processor" information.

World Wide Web thermometric.com/calorimetry, Jul. 27, 1998 "Caloimetry" information.

World Wide Web mettler.com, Aug. 10, 1998 "Automatic Laboratory Reactors, Reaction Calorimeters and On–line Analysis" information.

World Wide Web calscorp.com/about_csc, Feb. 8, 1999 "About Calorimetry Sciences Corp." information.

PCT/ISA/206, Invitation to Pay Additional Fees in Int'l Application No. PCT/US99/18358, Annex p. 1, Document Citation WO 98 57740 A, May 16, 2000.

PCT/ISA/220, Notification of Transmittal of the International Search Report in Int'l Application No. PCT/US99/18358, Sep. 25, 2000, and attached International Search Report.

"Heated Reacto—Stations," Estem Corporation, Oct. 1997.

"MultiReactor—Reactor Block," RoboSynthon, Inc.

J–KEM ® Scientific, Inc. "Reaction Blocks" information.

Randhava R., *Advanced Configurations for Catalyst Research*, Chemical Engineering Progress, Nov. 1983, pp. 52–58, vol. 70 No. 11, American Institute of Chemical Engineers, New York.

Ahrweiler, P., et al., "Automation of Parallel Synthesis From Reagent Preparation Through Sample Workup," *Am. Lab.* 1997, 29, 12–14.

Baselt, J.P., et al., "Microreactor Technology: Focusing the German Activities in this Novel and Promising Field of Chemical Process Engineering," 1997, pp. 13–17.

Buhlmann, R., et al., "An Open Software Environment to Optimize the Productivity of Robotized Laboratories," *J. Chromatogr. Sci.* 1994, 32, 243–248.

Cargill, J.F., et al., *Lab. Rob. Autom.* 1996, 8, 139–148 "Automated Combinatorial Chemistry on Solid Phase".

Corkan, A., et al., "Application of an Automated Chemistry Workstation to Problems in Synthetic Chemistry," *Chemom. Intell. Lab. Syst.* 1992, 17, 95–105.

Corkan, A., et al., "Design Concepts for Synthetic Chemistry Workstations," *Adv. Lab. Autom. Rob.* 1990, 6, 477–497.

Corkan, et al., "Experiment Manager Software for an Automated Chemistry Workstation, including a Scheduler for Parallel Experimentation," *Chemometrics and Intelligent Laboratory Systems: Laboratory Information Management*, 17 (Oct. 1992), No. 1, 47–74, Elsevier Science Publishers B.V., Amsterdam.

Gehrer, E., et al., "A Fully Programmable System for the Study of Catalytic Gas Reactions," *J. Phys. E: Sci. Instrum.* 1985, 18, 10, 836–838.

Hlavay, J. and Gullbault, G.G., "Applications of the Piezoelectric Crystal Detector in Analytical Chemistry," *Analytical Chemistry*, Nov. 1977, vol. 49, No. 13.

Josses, P., et al., "Carrying Out Multiple Reactions in Organic Synthesis with a Robot" *Adv. Lab. Autom. Rob.* 1990, 6, 463–475.

Kanazawa, K. Keiji and Gordon, Joseph G., "The Oscillation Frequency of a Quartz Resonator in Contact with a Liquid," *Analytica Chemica Acta*, vol. 175, pp. 99–185.

Kiezel, L., et al., *Chem. Stosow.* 1968, 12, 407–415.

Kipling, A.L., Thompson, M., "Network Analysis Method Applied to Liquid–Phase Acoustic Wave Sensors," *Analytical Chemistry*, 1990, vol. 62, pp. 1514–1519.

Li, K.T., et al., "Mixing and Control of a CSTR with Series–Parallel Reactions," *J. Chin. Inst. Chem. Eng.* 1991, 22, 61–69.

Lindsey, J.S., "A Retrospective on the Automation of Laboratory Synthetic Chemistry," *Chemom. Intell. Lab. Syst.* 1992, 17, 15–45.

McFarlane, R.C., et al., "Adaptive Optimizing Control of Multivariable Constrained Chemical Processes. 2. Application Studies," *Ind. Eng. Chem. Res.* 1989, 28, 1834–1845.

Michels, A., Meinen, F., Murdfield, T., Gohde, W., Fischer, U.C., Beckmann, E. and Fuchs, H., "1 MHz quartz length extension resonator as a probe for scanning near–field acoustic microscopy," *Thin Solid Films*, 1995, vol. 264, pp. 172–195.

Muramatsu, H., Kumura, K. Ataka, T., Homma, Y. Miura and Karube, I., "A Quartz Crystal Viscosity Sensor for Monitoring Coagulation Reaction and its Application to a Multichannel Coagulation Detector," *Biosensors & Bioelectronics*, 1991, vol. 6, pp. 353–358.

Muramatsu, H., Tamiya, Eiichi and Karube, Isao, "Computation of Equivalent Circuit Parameters of Quartz Crystals in Contact with Liquids and Study of Liquid Properties," *Analytical Chemistry*, 1988, vol. 60, pp. 2142–2146.

Nomura, T. and Iijima, M., "Electrolytic Determination of Nanomolar Concentrations of Silver in Solution with a Piezoelectric Quartz Crystal," *Analytica Chemica Acta*, 1981, vol. 131, pp. 97–102.

Plouvier, J.C., et al., "Experiment Planner for Strategic Experimentation with an Automated Chemistry Workstation," *Chemom. Intell. Lab. Syst.* 1992, 17, 75–94.

Salvet, M., et al., *Chem. Abstr.* 1997, 126, abstract 200993h.

Takamatsu, T., et al., "Optimal Scheduling and Minimum Storage Tank Capacities in a Process System with Parallel Batch Units," *Comput. Chem. Eng.* 1979, 3, 185–195.

* cited by examiner

Fig. 1B

|  | $R_1$ | $R_2$ | $R_3$ | $R_4$ | $R_5$ | $R_6$ | $R_7$ | $R_8$ | ...$R_N$ |
|---|---|---|---|---|---|---|---|---|---|
| $SV_1$ | X | X | X | X | X | X | X | X | X |
| $SV_2$ | X | X | X | X | X | X | X | X | X |
| $SV_3$ | X | X | X | X | X | X | X | X | X |
| $SV_4$ | X | X | X | X | X | X | X | X | X |
| $SV_5$ | X | X | X | X | X | X | X | X | X |
| $SV_6$ | X | X | X | X | X | X | X | X | X |
| $SV_7$ | X | X | X | X | X | X | X | X | X |
| $SV_N$ | X | X | X | X | X | X | X | X | X |

Fig. 1C

|  | $R_1$ | $R_2$ | $R_3$ | $R_4$ | $R_5$ | $R_6$ | $R_7$ | $R_8$ | ...$R_N$ |
|---|---|---|---|---|---|---|---|---|---|
| $SV_1$ | X | X | X | X |  |  |  |  |  |
| $SV_2$ | X | X | X | X |  |  |  |  |  |
| $SV_3$ | X | X | X | X |  |  |  |  |  |
| $SV_4$ |  |  | X | X | X | X |  |  |  |
| $SV_5$ |  |  | X | X | X | X |  |  |  |
| $SV_6$ |  |  |  |  | X | X | X | X | X |
| $SV_7$ |  |  |  |  | X | X | X | X | X |
| $SV_N$ |  |  |  |  | X | X | X | X | X |

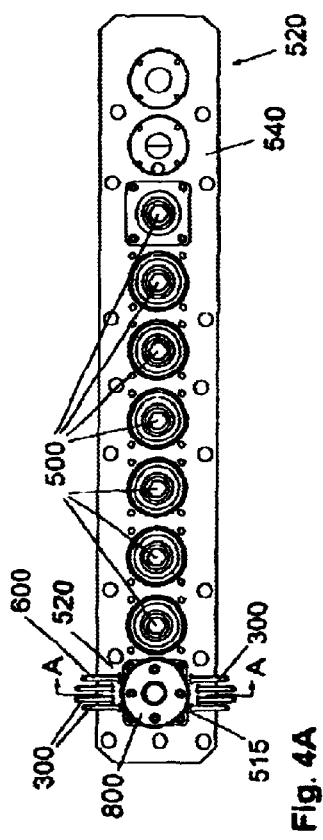
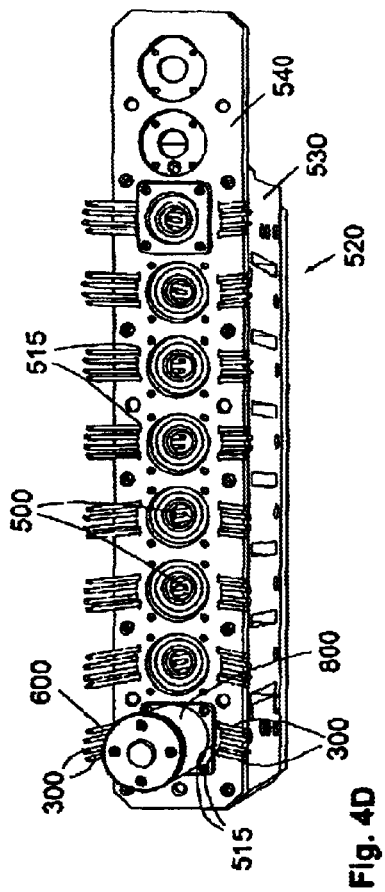
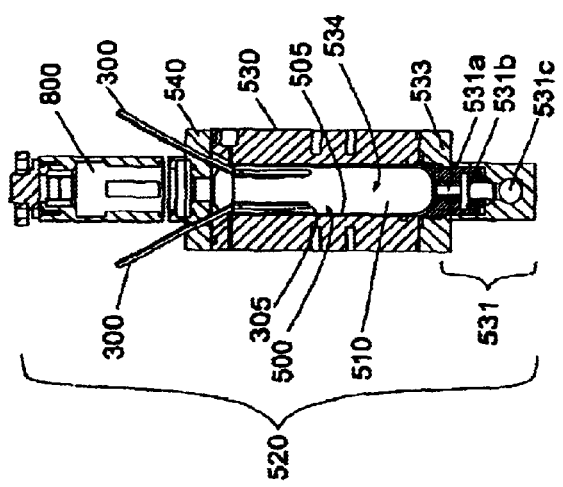

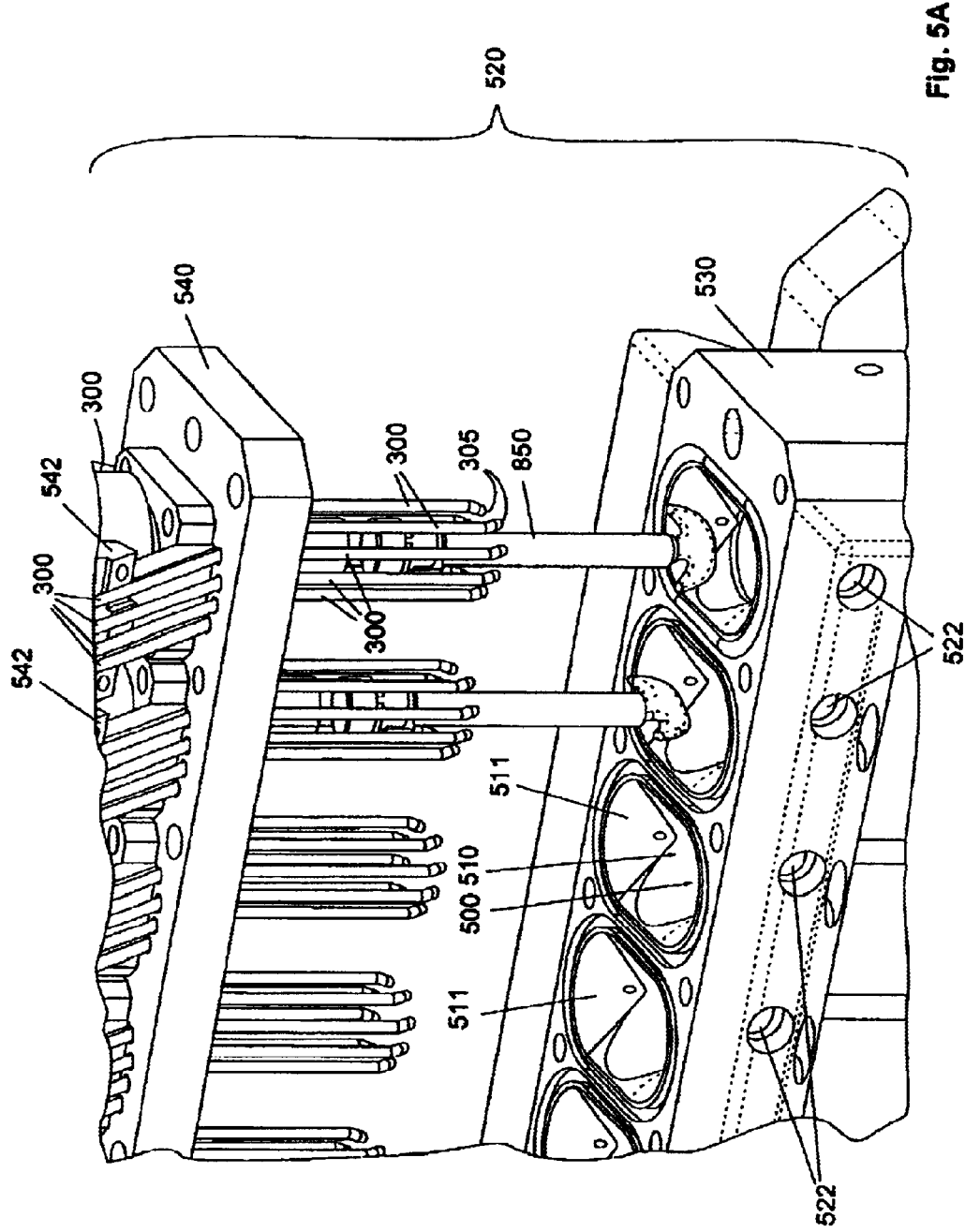

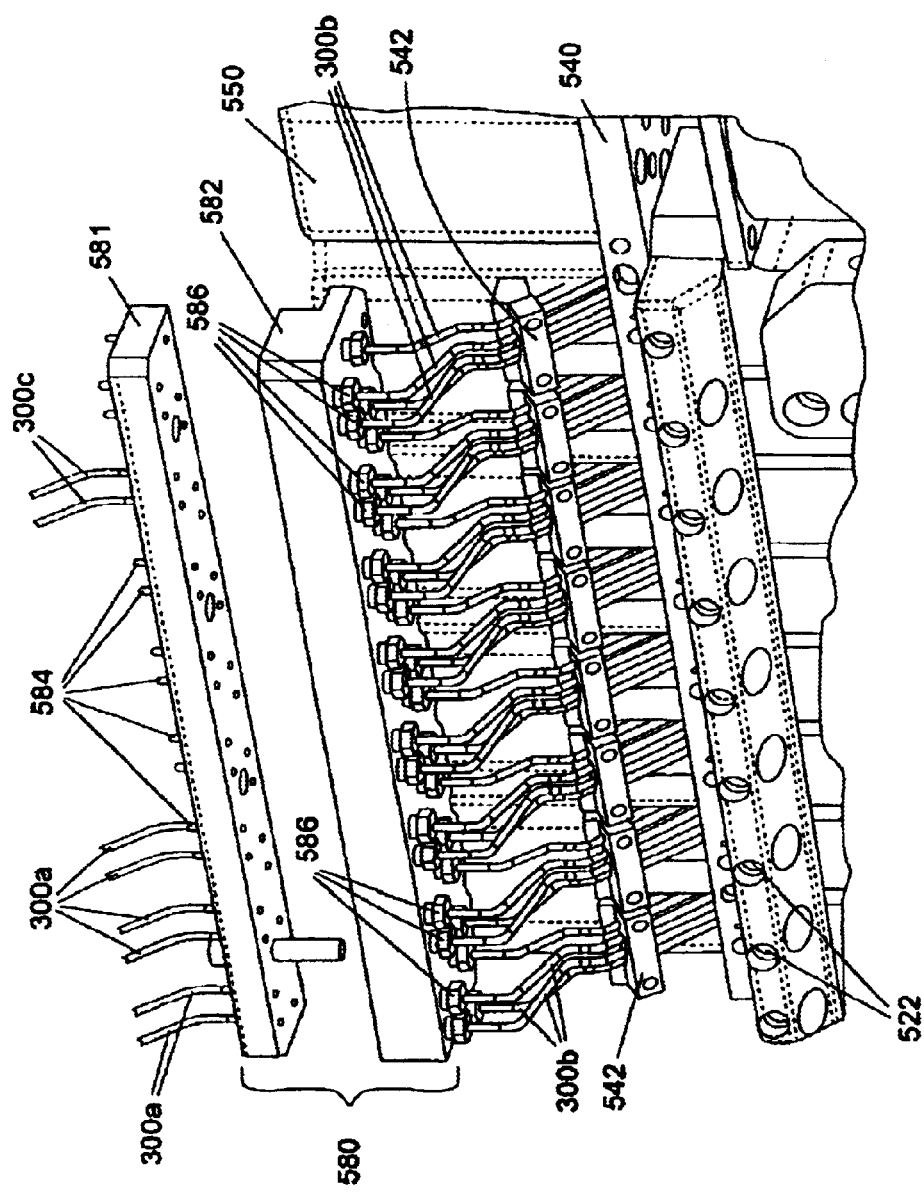

PARALLEL SEMICONTINUOUS OR CONTINUOUS REACTORS

The present invention is directed to parallel reactors, and in particular, to parallel research reactors suitable for use in a combinatorial (i.e., high-throughput) materials science research program. The invention is directed, in particular, to parallel semicontinuous or continuous reactors, and in preferred embodiments, to parallel semicontinuous or continuous stirred reactors. The invention is also directed to methods of using such parallel reactors for synthesis and/or screening of materials or process conditions, to methods for synthesizing combinatorial libraries of materials, and to methods for screening combinatorial libraries of materials, such as catalysts.

BACKGROUND

The present invention is related to the following co-owned, U.S. patent applications, each of which is hereby incorporated by reference for all purposes: U.S. Ser. No. 60/255,716 filed Dec. 14, 2000 by Safir et al., entitled "Parallel Semicontinuous or Continuous Stirred Reactors"; U.S. Ser. No. 60/209,142 filed Jun. 3, 2000 by Safir et al., entitled "Parallel Semicontinuous or Continuous Stirred Reactors"; U.S. Ser. No. 09/177,170 filed Oct. 22, 1998 by Turner et al., entitled "Parallel Reactor with Internal Sensing and Method of Using Same", now U.S. Pat. No. 6,548,026, issued Apr. 15, 2003; U.S. Ser. No. 09/211,982 filed Dec. 14, 1998 by Turner et al., entitled "Improved Parallel Reactor with Internal Sensing", now U.S. Pat. No. 6,306,658, issued Oct. 23, 2001; U.S. Ser. No. 09/548,848 filed Apr. 13, 2000 by Turner et al., entitled "Parallel Reactor with Internal Sensing and Method of Using Same", now U.S. Pat. No. 6,455,316, issued Sep. 24, 2002; U.S. Ser. No. 09/239,233 filed Jan. 29, 1999 by Wang et al., entitled "Analysis and Control of Parallel Chemical Reactions", now U.S. Pat. No. 6,489,168, issued Dec. 3, 2002; U.S. Ser. No. 09/205,071 filed Dec. 4, 1998 by Freitag et al., entitled "Continuous Feed Parallel Reactor", now U.S. Pat. No. 6,485,692, issued Nov. 26, 2002; U.S. Ser. No. 09/174,856 filed Oct. 19, 1998 by Lacy et al., entitled "Graphic Design of Combinatorial Material Libraries"; U.S. Ser. No. 09/420,334 filed Oct. 18, 1999 by Lacy et al., entitled "Graphic Design of Combinatorial Material Libraries"; and U.S. Ser. No. 09/305,830 filed May 5, 1999 by Rust et al., entitled "Synthesizing Combinatorial Libraries of Materials", now U.S. Pat. No. 6,507,945, issued Jan. 14, 2003.

The aforementioned related applications disclose a number of embodiments for parallel research reactors suitable for use, for example, in combinatorial chemistry applications such as polymer research and catalyst research.

In particular, U.S. application Ser. No. 09/177,170, U.S. Ser. No. 09/211,982, and U.S. Ser. No. 09/548,848 applications disclose a parallel pressure reactor (PPR™) having modular parallel, stirred reactors with temperature and pressure control. U.S. Ser. No. 09/239,233 discloses methodologies and software for controlling such parallel reactors. Although such parallel reactors can be advantageously applied for many polymer research applications (synthesis or screening of materials), the disclosed reactor systems have only limited capabilities for providing multiple reactants to the reaction vessel during the reaction.

Additionally, U.S. Ser. No. 09/205,071 discloses a parallel research reactor that can be adapted for semi-continuous (i.e., semi-batch) or continuous flow operation with one or more feed streams provided to each reactor. Although such a parallel reactor can be advantageously applied for polymer research applications and other research applications requiring semicontinuous or continuous feed, improvements in the disclosed multiple-feed capabilities are desirable, particularly with respect to higher-pressure applications.

Other parallel synthesis reactors are known in the art, particularly in applications directed toward the synthesis of biological polymers (e.g. nucleic acid polymers such as oligonucleotides, or amino acid polymers such as peptides or proteins) or small organic molecules (e.g., having potential pharmaceutical or diagnostic uses), and especially solid-phase synthesis of such compounds. See, for example, U.S. Pat. No. 5,746,982 to Saneii et al., PCT patent application WO 98/13137 of Antonenko et al., European patent application EP 963 791 A2 of Harness et al., PCT patent application WO 97/10896 of Mohan et al., PCT patent application WO 90/02605 of Meldal et al., European patent application EP 658 566 A1 of Chatelain et al., and U.S. Pat. No. 5,792,431 to Moore et al. A system for parallel dissolution testing (e.g., for pharmaceutical compositions) is also known. See, for example, European patent application EP 635 713 A1 of Hutchins et al. These parallel research reactors and other instruments are not, however, generally useful for polymerization research—typically involving higher temperatures, higher pressures and/or in some cases, non-aqueous solvents Moreover, such reactors have limited feed capability during the reaction, and as such, are not generally adaptable for semi-continuous operation with multiple feed streams.

In addition to the aforementioned limitations associated with particular designs, known parallel reactor designs generally suffer from common deficiencies—particularly with respect to applications for polymer research or other applications. In general, known designs are substantially limited with respect to operational flexibility, and do not generally offer higher numbers of feed lines per reactor in combination with desirable higher pressures, higher temperatures, and effective stirring (for polymerization reaction mixtures), in a semicontinuous or continuous operational mode. In particular, the known reactor designs are spatially constrained, and offer limited flexibility for incorporating larger number of feed lines to a relatively small volume reactors. Further, assembly and/or disassembly of the systems (e.g., for reactor vessel access) are relatively complicated, and would result in significant "down time" during an experimental cycle. Moreover, the known designs do not advantageously provide the desired control of feed addition (e.g. feeding of precise, incremental amounts of reagents) to the reaction vessel during a reaction under reaction conditions. Finally, the known parallel reactors offer only moderate flexibility, if any, with respect to evaluating process/protocol parameter space involving multiple reactants—including the sequence, total volume, rate, and temporal profile of reactant addition to a reaction vessel.

SUMMARY OF THE INVENTION

It is therefore an object of the present invention to overcome the deficiencies of known parallel reactors, and especially known parallel research reactors. In particular, it is an object of the invention to provide apparatus, methodologies, and software (or firmware) that will enable a research scientist to effect simultaneous reactions in a parallel reactor system having multiple feeds, with efficient stirring for polymerization reaction mixtures and with substantial flexibility for feed configuration, reaction conditions, and feed-protocols.

Briefly, therefore, the present invention is directed, in one embodiment, to a parallel reactor, and especially to a parallel research reactor suitably configured for operation in semicontinuous or continuous mode. The parallel reactor comprises two or more, preferably four or more reaction vessels for containing liquid reaction mixtures. Each of the two or more (or four or more) reaction vessels can have a volume of not more than about 1 liter, preferably not more than about 500 ml, and is pressurizable to a pressure of not less than about 50 psig (i.e., is hermetically sealed), preferably not less than about 100 psig, preferably not less than about 1000 psig. Although pressurizable to higher pressures, the apparatus has significant applications at atmospheric pressure. The two or more, and preferably four or more reaction vessels are preferably integral with (e.g. formed or otherwise contained in) a common reactor block. In some embodiments, however (e.g., with volumes of not more than about 1 liter), the reaction vessels can be configured independently of each other (e.g. without being formed in a common reactor block). Two or more (or four or more) shaft-driven stirrers (e.g., shaft-driven impellers) can be provided for stirring the reaction mixtures. The shaft-driven stirrers (e.g. impellers) are, if provided, preferably arranged to correspond to the arrangement of the two or more (or four or more) reaction vessels. The reactor vessel further comprises at least two, preferably at least three, and more preferably at least four feed lines (e.g., liquid feed lines) in fluid communication with each of the two or more (or four or more) reaction vessels. Each of the at least three (or at least four) feed lines provide fluid communication, preferably selective fluid communication, between the reaction vessel and one or more reagent sources (e.g. liquid reagent sources).

In preferred embodiments, the invention is directed to a parallel reactor (e.g., as described in the preceding paragraph), or to a reactor having a single reaction vessel, in either case configured for semi-continuous or continuous operation, that includes certain features (considered independently, in combination with the above embodiment, and/or in various combinations with each other) that enhance the functionality or efficiency of a multi-feed system, and/or that improve the control of feed addition to the reaction vessel(s). Briefly, such features include, without limitation, a feed-pressurization station (e.g., pressurized waste vessel), one or more modular feed-line subassemblies (e.g. ferrules), capillary-type feed lines, multi-section (e.g., two-section) feed lines, multiple feed lines with independently and differently-positioned distal ends, feed lines with independently and differently-varied feed-line sizes, disposable shaft-covers and/or disposable header block gaskets for masking at least non-disposable portions of the shafts or header that are exposed within the reaction cavity and/or specific feed distribution system designs, including especially feed distribution systems in which one or more source vessels are multiplexed through a single pump (e.g., syringe pump) and one or more selection valves (e.g., feed distribution valves), to each of multiple feed lines serving multiple reaction vessels. Such features are briefly summarized in more detail as follows, and further described below.

In one such preferred embodiment, a feed-pressurization station (e.g., pressurized waste vessel) is in selectable fluid communication with the feed line(s) such that the feed line(s) can be prepressurized—prior to feeding reagents to the reaction vessel(s)—by prefeeding the liquid reagent(s) to the feed-pressurization station under pressure, preferably under pressure that is substantially the same as the reaction pressure.

In another such embodiment, for example, the invention includes one or more modular feed-line subassemblies (e.g. ferrules), with each of the feed-line subassemblies being adapted to releasably engage a reaction vessel or a reactor block having a reaction cavity that defines or contains the reaction vessel. The feed-line subassembly supports at least two feed lines (and preferably at least three or at least four feed lines) passing into the reaction vessel through a feed-line subassembly receiving port that is formed in the reaction vessel or the reactor block.

In an additional such embodiment, the feed lines are capillary feed lines (e.g., glass (e.g., fused silica) capillaries, stainless-steel capillaries and/or polymer (e.g. teflon) capillaries).

In another such embodiment, one of, or preferably each of, the at least two, at least three (or at least four) liquid feed lines are multi-section feed lines, having at least a first section and a second section in fluid communication with each other. Preferably, the second section is releasably engaged with the first section and has a distal end positioned within the reaction vessel or within a reaction cavity or reaction chamber that defines or contains the reaction vessel.

In an additional such embodiment, each of the at least two, at least three (or at least four) liquid feed lines has a distal end positioned within the reaction vessel, and the distal end of one or more of the feed lines (i.e., a first subset of the feed lines) is positioned lower in the reaction vessel relative to the distal end of one or more other of the feed lines (i.e., a second subset of the feed lines). Such an approach is particularly advantageous with respect to delivery of some of the reagents directly into the a liquid reaction mixture and some other reagents into a gaseous headspace above the liquid reaction mixture.

In a further such embodiment, each of the at least two, at least three (or at least four) liquid feed lines has an inside diameter or cross-sectional flow area, and one or more of the at least three (or at least four) liquid feed lines (i.e., a first subset of the feed lines) has an inside diameter or cross-sectional flow area that differs from the inside diameter or cross-sectional flow area for another of the at least four liquid feed lines (i.e., a second subset of the feed lines).

In yet a further such embodiment, the various components within the reaction cavity that are exposed to the reaction conditions are either disposable (e.g. disposable vials as reaction vessels, disposable feed-line sections, disposable impellers) and/or are masked from the reaction environment by gaskets (e.g. header gasket having masking regions) covers (e.g., shaft covers) or other masking materials—with such masking materials themselves being disposable.

The invention is likewise directed to methods for using the any of the aforementioned apparatus to effect multi-feed chemical reactions in parallel—generally by feeding three or more (or four or more) liquid reagents through the three or more (or four or more) feed lines to each of the two or more (or four or more) reactors during the course of a reaction.

The invention is directed as well to methods for effecting multi-feed chemical reactions in parallel. In general, the methods include providing one or more of the aforementioned single and/or parallel reactors, and feeding, preferably selectively feeding, one or more liquid reagents through the one or more (e.g., two or more, three or more, four or more, etc.) feed lines to the reaction vessel(s) during a reaction under reaction conditions, preferably under reaction conditions that include a reaction pressure of not less than about 50 psig.

In one preferred embodiment, a parallel pressure reactor is provided. The parallel pressure reactor comprises two or more, preferably four or more semi-continuous or continuous reaction vessels, one or more liquid reagent source vessels, and at least two, preferably four liquid feed lines providing selectable fluid communication between the one or more liquid reagent source vessels and the four or more reaction vessels. A chemical reaction is initiated in each of the four or more reaction vessels under reaction conditions that include a reaction pressure of not less than about 50 psig. One or more liquid reagents are prefed through one or more of the at least four feed lines to a feed-pressurization zone—preferably a pressurized waste vessel. The feed-pressurization zone is maintained at a pressure of not less than about 50 psig, and preferably at a pressure that corresponds substantially to the reaction pressure, such that the feed lines contain prepressurized liquid reagent feed. The prepressurized liquid reagent feed is then subsequently fed into one or more of the two or more, or four or more reactor vessels during the reaction under the reaction conditions.

Additionally, and generally, such methods are preferably implemented with user-directed reactor-control software or firmware incorporated with the reactor, together with a graphical user interface. The feed control effected, preferably with such software or firmware, is preferably applied in connection with methods in which a parallel reactor is provided and comprises four or more semi-continuous or continuous reaction vessels, four or more liquid reagent source vessels, and at least four liquid feed lines providing selectable fluid communication between the four or more liquid reagent source vessels and the four or more reaction vessels. A chemical reaction is initiated in each of the four or more reaction vessels under reaction conditions, and the four or more liquid reagents are fed into the four or more reaction vessels during the reaction under the reaction conditions. Significantly, the feed control, for each of the reaction vessels, can include controlling (e.g., specifying and/or directing) (i) a total volume of each of the liquid reagents being fed to the reaction vessel during the reaction, the total volume being the same or different as compared between different reagents, (ii) a number of stages in which the total volume for each of the liquid reagents are fed to the reaction vessel during the reaction, the number of stages being the same or different as compared between different reagents, (iii) a stage volume defined by a percentage of the total volume associated with each of the stages for each of the liquid reagents, the stage volume being the same or different as compared between different stages for each of the liquid reagents, (iv) a feed sequence defined by a relative order in which the stages for each of the liquid reagents are fed to the reaction vessel during the reaction, and (v) a temporal profile associated with feed addition to the reaction vessel for each of the stages for each of the liquid reagents, the temporal profile being defined for each stage by a number of feed increments in which the stage volume is added to the reaction vessel, and the period of time in which the stage volume is added to the reaction vessel.

The feed addition is preferably controlled, as considered between reaction vessels, sequentially, on a rotating basis, for each of the four or more reaction vessels during the reaction by (i) considering and providing the feed requirements for a first reaction vessel at a first time after initiation of the chemical reaction therein, and thereafter, (ii) by considering and providing the feed requirements for a second reaction vessel at a second time after initiation of the chemical reaction therein, and thereafter, (iii) by considering and providing the feed requirements for a third reaction vessel at a third time after initiation of the chemical reaction therein, and thereafter, (iv) by considering and providing the feed requirements for a fourth reaction vessel at a fourth time after initiation of the chemical reaction therein.

Advantageously, the present invention overcomes many deficiencies of the prior art. In particular, the multiple-feed reactors of the present invention offer substantial simplicity in design, and afford efficient, effective assembly and disassembly for access to the reaction vessel(s). Moreover, unique design features enable a multiple feed configuration suitable for spatially constrained reactors—such as relatively small volume reactors having shaft-driven stirring—even for relatively higher numbers of feed lines per reactor. The instant inventions also provide substantial flexibility and control over the nature of the feed addition to the reaction vessel. Furthermore, the parallel reactors disclosed herein are especially advantageous with respect to applications involving evaluation of process/protocol parameter space involving multiple reactants—including without limitation, the sequence, total volume, rate, and temporal profile of reactant addition to a reaction vessel, together with temperature profiles and/or pressure profiles.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references arc available to a skilled artisan that will provide further instruction with respect to such subject matter.

The invention is described in further detail below with reference to the attached figures, in which like items are numbered the same in the several figures.

BRIEF DESCRIPTION OF THE DRAWINGS

FIG. 1B is a schematic of the reactor of FIG. 1A illustrating each feed channel being in independent fluid communication with each reaction vessel;

FIG. 1C is a schematic of the reactor of FIG. 1A illustrating various subsets of the feed channels being in independent fluid communication with various subsets of the reaction vessels;

FIG. 2G is schematic of another embodiment of the feed distribution system of the present invention having dedicated distribution pumps and dedicated distribution valves providing dedicated reagent distribution;

FIG. 4A is a top plan view of a reactor block of the present invention;

FIG. 4B is a section of the reactor block of FIG. 4A taken through the line A—A of FIG. 4A;

FIG. 4D is a perspective of the reactor block of FIG. 4A;

FIG. 5A is an enlarged, exploded, fragmentary perspective of the reactor block of FIG. 4H;

FIG. 6A is an enlarged perspective of a reactor and a parallel feed-line interface of the present invention.

DETAILED DESCRIPTION OF THE INVENTION

Although described herein primarily in connection with applications involving chemical reactions, the reaction system can be a more general chemical processing system suitable for use with other chemical operations, that may not necessarily involve the making or breaking of a chemical bond. Such other applications, include, for example, the preparation of formulations, blending operations, and crystallization operations (e.g., for combinatorial investigations of polymorphic crystalline structures, among other applications).

Overview

The parallel reactor system of the present invention provides for a semicontinuous flow regime, or in an alternative embodiment, a continuous flow regime, for a number ("n", where n≧2, and preferably n≧4) of reaction vessels configured for parallel operation (e.g., configured for operation with at least four simultaneous reactions in at least four different reaction vessels, and ranging from four to "n" simultaneous reactions in from four to "n" different reaction vessels, respectively).

Figure 1A:
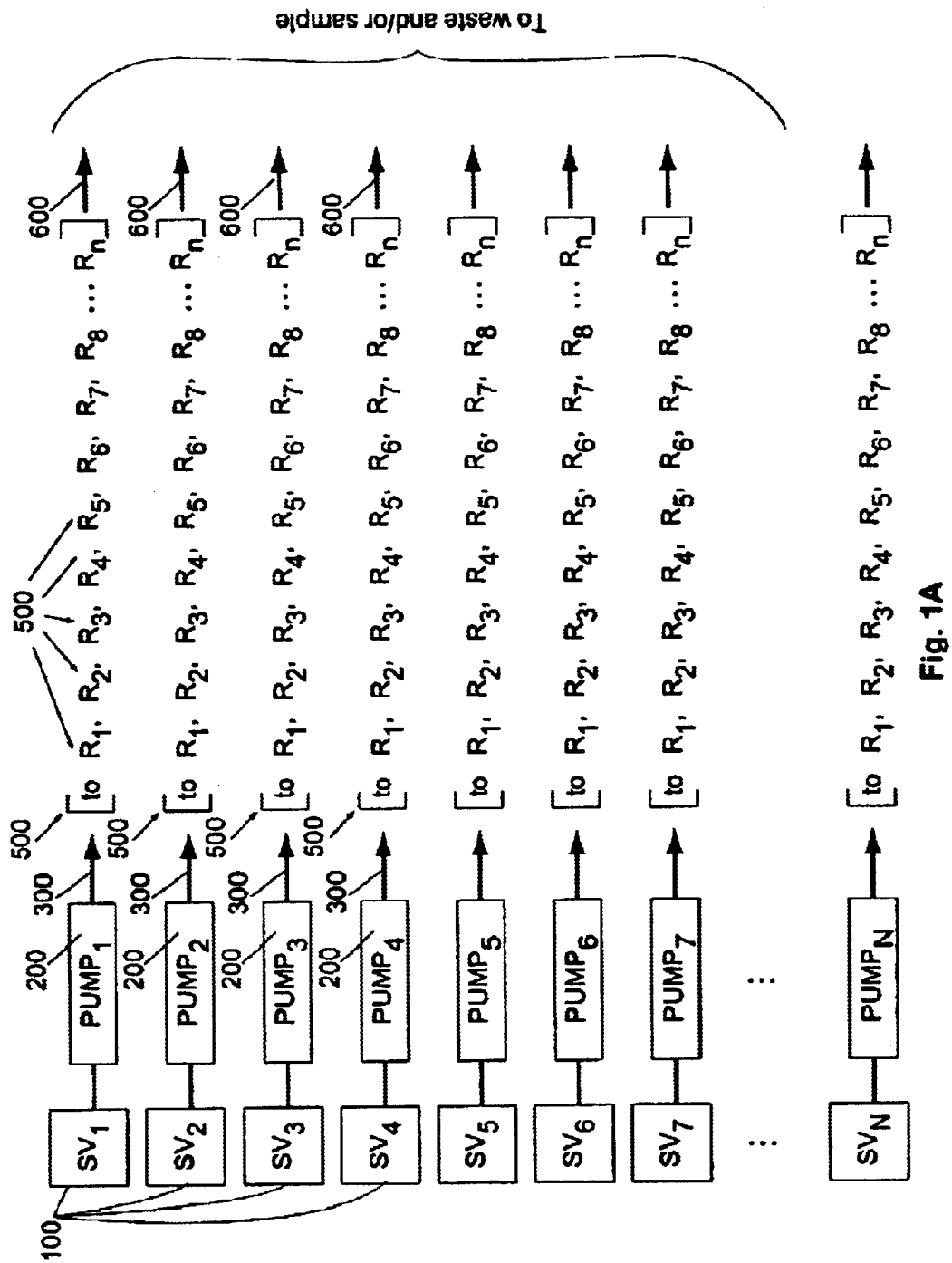
FIG. 1A is a schematic of one embodiment of a reactor of the present invention illustrating a semicontinuous or continuous flow regime having N number of reaction vessels.

In a semicontinuous flow embodiment, with reference to FIG. 1A, a number ("N", where N≧2) of feed lines 300 are provided to each of the n reaction vessels (represented schematically in FIG. 1 as a collective group of reaction vessels [$R_1, R_2, R_3, R_4, R_5, R_6, R_7, R_8 \ldots R_n$] and indicated generally as 500) such that each of N reagent can be added (e.g. intermittently) to each of the n reaction vessels 500 during the course of the reactions occurring in each of the n reaction vessels 500. A feed distribution system comprising the N feed lines 300 provides fluid communication between each of N different reagent source vessels 100 (labeled schematically in FIG. 1A as $SV_1$ through $SV_N$) and each of the n reaction vessels 500, typically through N dedicated pumps 200. In the semicontinuous embodiment, the n reaction vessels 500 are semi-batch reactors lacking a continuous discharge line (or alternatively, at least operated as semi-batch reactor, for example, with a discharge line valved shut, optionally except for intermittent sampling), such that substantially none of the reaction mixture is discharged from the reaction vessel during the course of the reaction.

In a continuous flow embodiment, with reference again to FIG. 1A, a number ("N", where N≧2) of feed lines 300 are provided to each of the n reaction vessels (represented schematically in FIG. 1 as a collective group of reaction vessels [$R_1, R_2, R_3, R_4, R_5, R_6, R_7, R_8 \ldots R_n$] and indicated generally as 500) such that each of N reagents can be added (e.g., intermittently) to each of the n reaction vessels 500 during the course of the reactions occurring in each of the n reaction vessels 500. A feed distribution system comprising the N feed lines 300 provides fluid communication between each of N different reagent source vessels 100 (labeled schematically in FIG. 1A as $SV_1$ through $SV_N$) and each of the n reaction vessels 500, typically through N dedicated pumps 200. In the continuous embodiment, the n reaction vessels 500 are continuous-flow reactors and a discharge distribution system provides fluid communication between each of the n reaction vessels is and at least one discharge line 600 such that at least a portion of the reaction mixture can be discharged (e.g., intermittently) from each of the n reaction vessels during the course of the reactions (e.g., to a common or to separate collection receptacle (e.g., waste receptacle) and/or a sample line).

In operation, in the semicontinuous flow or the continuous flow embodiments, the reagents from the N reagent source vessels 100 can be fed, through feed lines 300, to the n reaction vessels during the course of the reaction. The duration of feed can vary, and can be continuous over a period of time (i.e., temporally continuous) or intermittent over a period of time (i.e., temporally intermittent). In the continuous flow embodiment, a portion of the reaction mixture can be discharged from the reaction vessel during the course of the reaction, with the period of discharge varying in duration. The duration of the discharge can be temporally continuous, or temporally intermittent, and in some applications, can be temporally synchronized with the feeding of reagents (e.g. for operation as a continuous reactor, such as a continuous stirred tank reactor).

The number of reaction vessels and/or reagent source vessels (with associated dedicated feed channels) can vary for the parallel reactor system of the present invention. As noted above, the number of reaction vessels can be two or more, but is preferably at least about 4 and is more preferably about 8 or more reaction vessels. Higher numbers, n, of reaction vessels can be employed, including for example, 16 or more, 40 or more, 60 or more, 100 or more, 400 or more or 1000 or more. In some embodiments, the number of reaction vessels can be at least about 96*M, where M ranges from 1 to about 100, and preferably ranges from 1 to about 10, and most preferably ranges from 1 to about 5. The 4 or more reaction vessels can be independently positioned with respect to each other, or alternatively, can be formed in modules or in a monolith. The number, N, of feed channels associated with each of the n reaction vessels can, as noted above, be at least about 2, and in some embodiments, is preferably 3 or more, 4 or more, 5 or more, 6 or more, 7 or more, or 8 or more, and can range, for example, from 2 to about 20, preferably from 2 to about 10, more preferably from 3 to about 10, and most preferably from 4 to about 8.

The correspondence between the four or more reaction vessels and the two or more feed streams can be complete or, particularly with higher numbers of reaction vessels, n, and higher numbers of feed channels, N, such correspondence can be partial. With reference to FIG. 1B, for example, each of the N feed channels (indicated as N reagent source vessel, SV's) can be in independent fluid communication with each of the n reaction vessels. Alternatively, with reference to FIG. 1C, for example, various subsets of the N feed channels (each of the various subsets comprising at least 2 reagent source vessels and reagent feed channels) can be in independent fluid communication with various subsets of the n reaction vessels (each of the various subsets comprising at least four reaction vessels). The particular correspondence will be apparent to a person of skill in the art in view of the chemistry of interest being applied in the parallel reactor. Advantageously, in preferred embodiments, the parallel semicontinuous or continuous reactor of the present invention can be flexibly configured to have a first feed channel-reaction vessel correspondence, and then reconfigured to have a second feed channel-reaction vessel correspondence, completely by appropriate control of distribution valving included as part of the feed distribution system.

Feed Distribution Systems

The feed distribution system for either of the aforementioned semicontinuous embodiment or continuous embodiment can include a feed-line splitting arrangement or a feed-line valving arrangement that provides for fluid communication, preferably selectable fluid communication, between one of the reagent source vessels (e.g., $SV_N$) and each of the n reaction vessels.

Figure 2A:
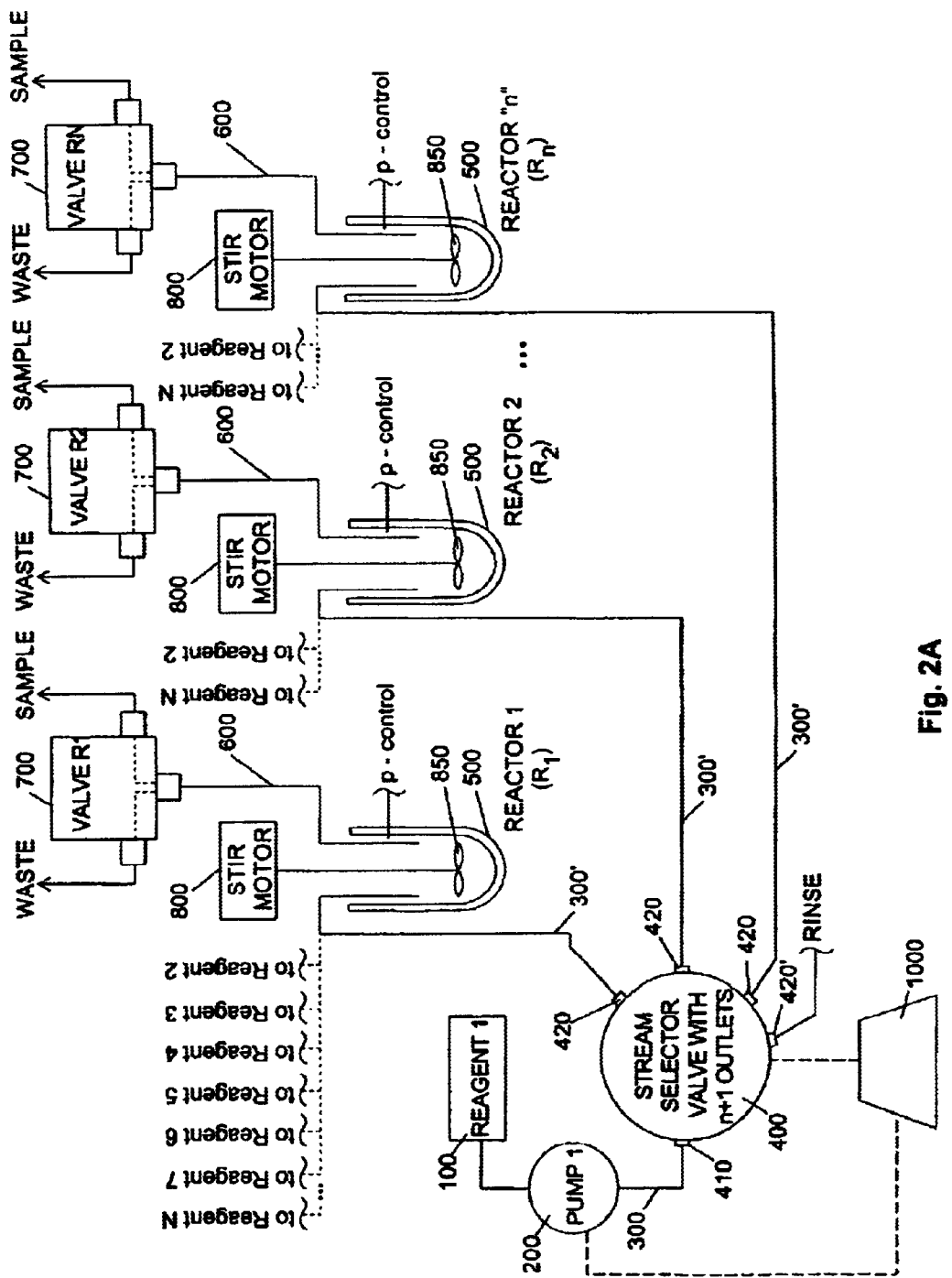
FIG. 2A is a schematic of one embodiment of a feed distribution system of the present invention illustrating selective fluid communication between one of the reagent source vessels and the reaction vessels selectively provided through a selection valve.

In a preferred feed distribution system, shown schematically in FIG. 2A, selective fluid communication between one of the reagent source vessels 100 and the n reaction vessels is selectively provided through a selection valve, designated herein as a feed distribution valve 400. Hence in operation, one of the N reagents is pumped by a dedicated distribution pump 200 from the reagent source vessel 100 through a common feed line 300 to a feed inlet 410 of the feed distribution valve 400. The feed distribution valve 400 is controlled (e.g., with microprocessor 1000) to selectively provide fluid communication between the feed inlet 410 and one (or more) of n feed outlets 420. Feed lines 300' provide fluid communication between each of the n feed outlets 420 and one of the n reaction vessels 500. Alternatively, where additional feed-branching is required (e.g., where n is sufficiently high), each of the feed lines 300' could themselves be in fluid communication with an additional selection valve (not shown), the outlets of which could be in fluid communication with the reaction vessels. One of the feed outlets 420' of the feed distribution valve 400 can be in fluid communication with a rinse collection vessel (e.g., for flushing the distribution valve), or alternatively a rinse source vessel. Although details of the feed distribution system as shown in FIG. 2A are depicted only for one of the N reagent feed channels (to each of the n reactors), each of the other reagent feed channels could be likewise configured with a selection valve (See FIG. 2B).

Figure 2B:
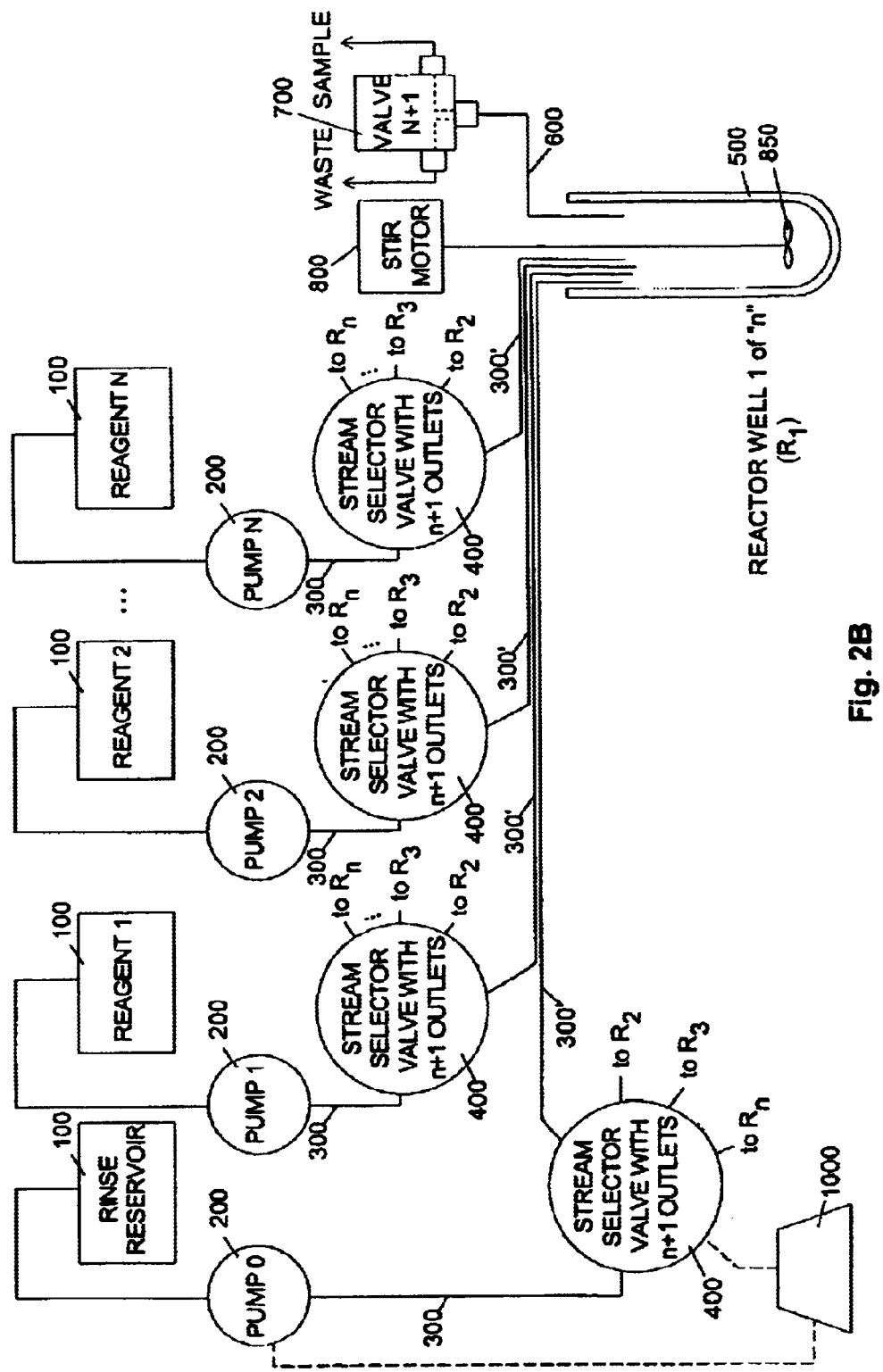
FIG. 2B is a schematic of the feed distribution system of FIG. 2A illustrating each reagent source vessel configured with a selection valve.
Figure 2C:
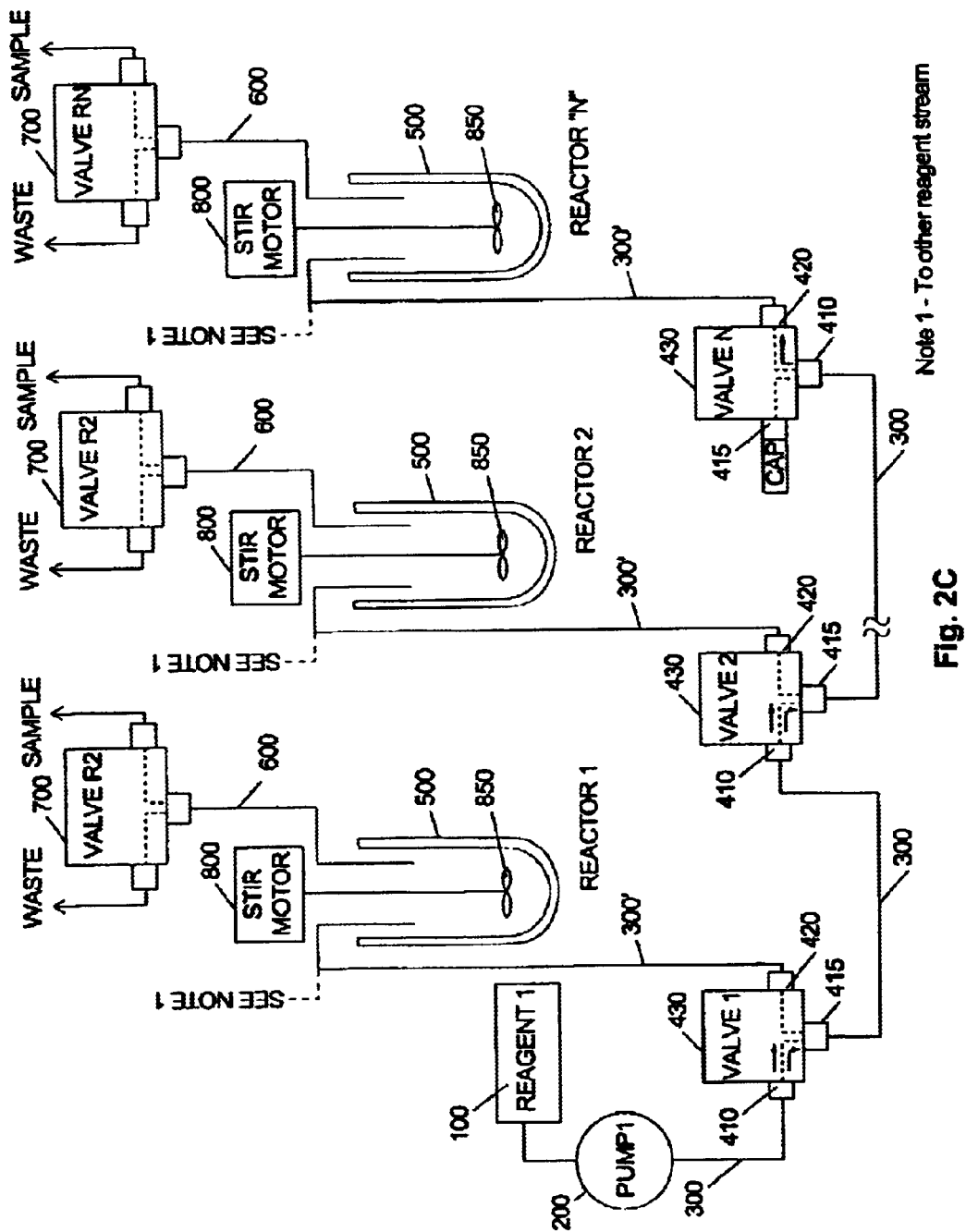
FIG. 2C is a schematic of another embodiment of the feed distribution system of the present invention illustrating a plurality of separate multi-way valves, each valve associated with a particular reagent.

An alternative feed distribution system, shown schematically in FIG. 2C, includes a plurality of separate multi-way valves 430 in place of the single, feed-line distribution valve. Reagent feed is fed from the reagent source vessel 100 through a pump 200 through a common feed line 300 to a feed inlet 410 of the multi-way valve 430. The multi-way valves 430 are each controlled (e.g., with a microprocessor, not shown) to selectively provide fluid communication between the feed inlet 410 and either a feed outlet 420 or a bypass outlet 415. The bypass outlet 415 of the last valve in the series can be capped. Feed lines 300' provide fluid communication between each of the n feed outlets 420 and one of the n reaction vessels 500.

In operation, the preferred feed distribution system (comprising at least one feed distribution valve for each of the N feed channels and having a dedicated distribution pump 200 associated with each reagent source vessel, as discussed in connection with FIG. 2A and FIG. 2B) or the alternative feed distribution system (discussed in connection with FIG. 2C) each offer substantial flexibility with respect to the addition of from two to N reagents to the n reaction vessels. For example, first and second reagents, reagent feeds 1 and 2, respectively, can be supplied simultaneously from their respective first and second reagent source vessels (SV1, SV2) to the same reaction vessel (e.g., $R_3$). Alternatively, the first and second reagents can be supplied at different times to the same reaction vessel. The same flexibility exists for each of the other reaction vessels. Hence, substantial operational flexibility is achieved with respect to control of reagent feed timing to one of the parallel reaction vessels. Moreover, such flexible control is achieved, independently, with respect to each of the other n reaction vessels.

Additionally, because each of the reagent feed channels preferably has its own dedicated distribution pump, and because each channel can be selectively fed to any of the n reactors, the aforementioned feed distribution systems advantageously provide for independently controlled rates of feed addition (for each reagent to each of the n reactors). Such control can be particular advantageous for combinatorial chemistry applications, in which feed rates and/or timing can affect the reaction in progress.

Figure 2D:
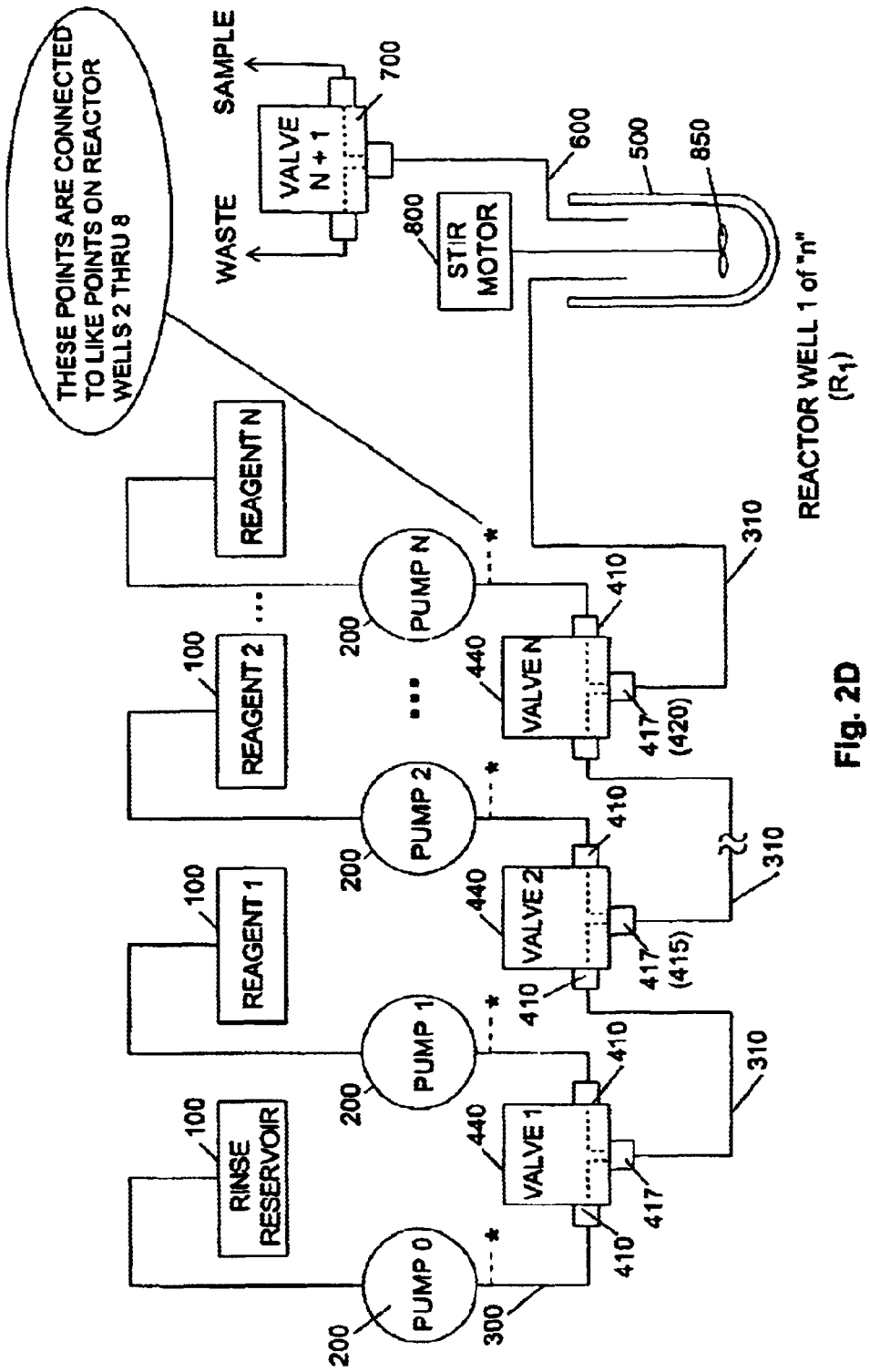
FIG. 2D is a schematic of another embodiment of the feed distribution system of the present invention illustrating in-line premixing of reagents in a common feed line.
Figure 2E:
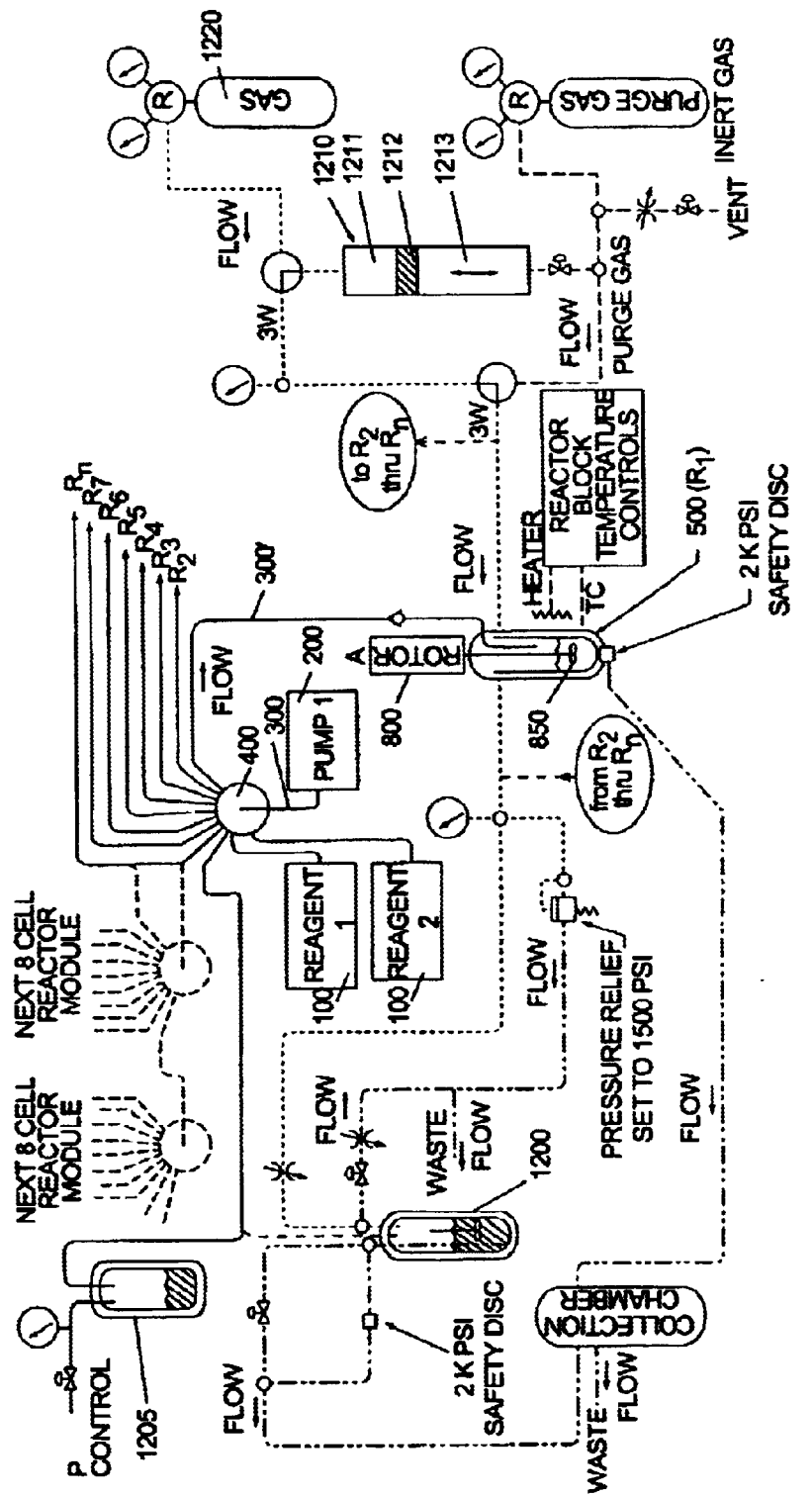
FIG. 2E is a schematic of another embodiment of the feed distribution system of the present invention having a single pump and selection valve servicing a plurality of different reagent source vessels.

In some cases, or for some reagent source vessels, it may nonetheless be advantageous to have one or more non-dedicated distribution pumps—that is, one or more pumps that service a plurality of different reagent source vessels (rather than having dedicated association with one reagent source vessel). With reference to FIG. 2E, for example, a single pump 200 such as a syringe-type pump can service a plurality of reagent source vessels 100 by aligning the pump with one or the other of the source vessels 100 through a selection valve The selection valve can be in-line on the inlet side of a flow-through pump (not shown), or alternatively, as shown in FIG. 2E, the selection valve can be a feed distribution valve 400 for pumps such as syringe-type pumps that have temporally separate intake and output modes. In operation for the latter case, the reagent in the aligned source vessel 100 can be taken up in the pump reservoir during the intake mode, and then discharged to the appropriate feed line 300' (i.e., to $R_1, R_2, \ldots R_n$) through the distribution valve 400 during the output mode. Although not shown in FIG. 2E, a similar configuration can be used to align a plurality of pumps 200 to one or more source vessels 100 through a common selection valve, such as distribution valve 400.

The feed distribution system preferably comprises separate dedicated feed channels for each of the N reagent feeds, where the feed channels are completely (or at least substantially) independent of each other, such that no substantial mixing of the feed streams occurs prior to being fed into the reactor. Such a configuration advantageously allows for delivery of different reagents to a particular reaction vessel where the reagents being added are chemically incompatible with each other (e.g., would react with each other if mixed prior to addition to the reaction vessel). Moreover, such a configuration also allows for delivery of reagents that would form a heterogeneous (i.e., two-phase) mixture if combined before delivery. If the two-phase mixture were non-uniform, the actual amount of each phase delivered to a reaction vessel would be difficult to control.

For chemical reaction applications where reagent compatibility and phase homogeneity between at least two reagents is not a substantial concern, an embodiment allowing for at least some pre-mixing of the at least two reagents can be effected. The reagents can be premixed, for example, in a mixing vessel (preferably comprising an active mixing element), and the mixture can then be distributed as a mixed-feed stream to the reaction vessel of interest. In an alternative pre-mixing approach, shown schematically in FIG. 2D, premixing can be effected "in-line" in a common feed line 310". The feed line 310 can be a passive mixer (e.g., comprising a tortuous mixing path). As depicted, the feed distribution system includes a plurality of separate multi-way mixing valves 440. Reagent feed is fed from the various reagent source vessels 100 through pumps 200 and feed lines 300 to a feed inlet 410 of the multi-way mixing valve 440. The multi-way mixing valves 440 are each controlled (e.g., with a microprocessor, not shown) to selectively provide fluid communication between the one or more feed inlets 410 and a mixed-feed outlet 417 or alternatively, a bypass outlet 415. The mixed-feed outlet 417 of the last valve in the series is also the feed outlet 420 for the series of valves.

Fluid communication between reagent source vessels (e.g., $SV_N$) and some or each of the n reaction vessels can, in general, be provided by any suitable approach, and the aforementioned embodiments are to be considered exemplary and non-limiting.

Figure 2F:
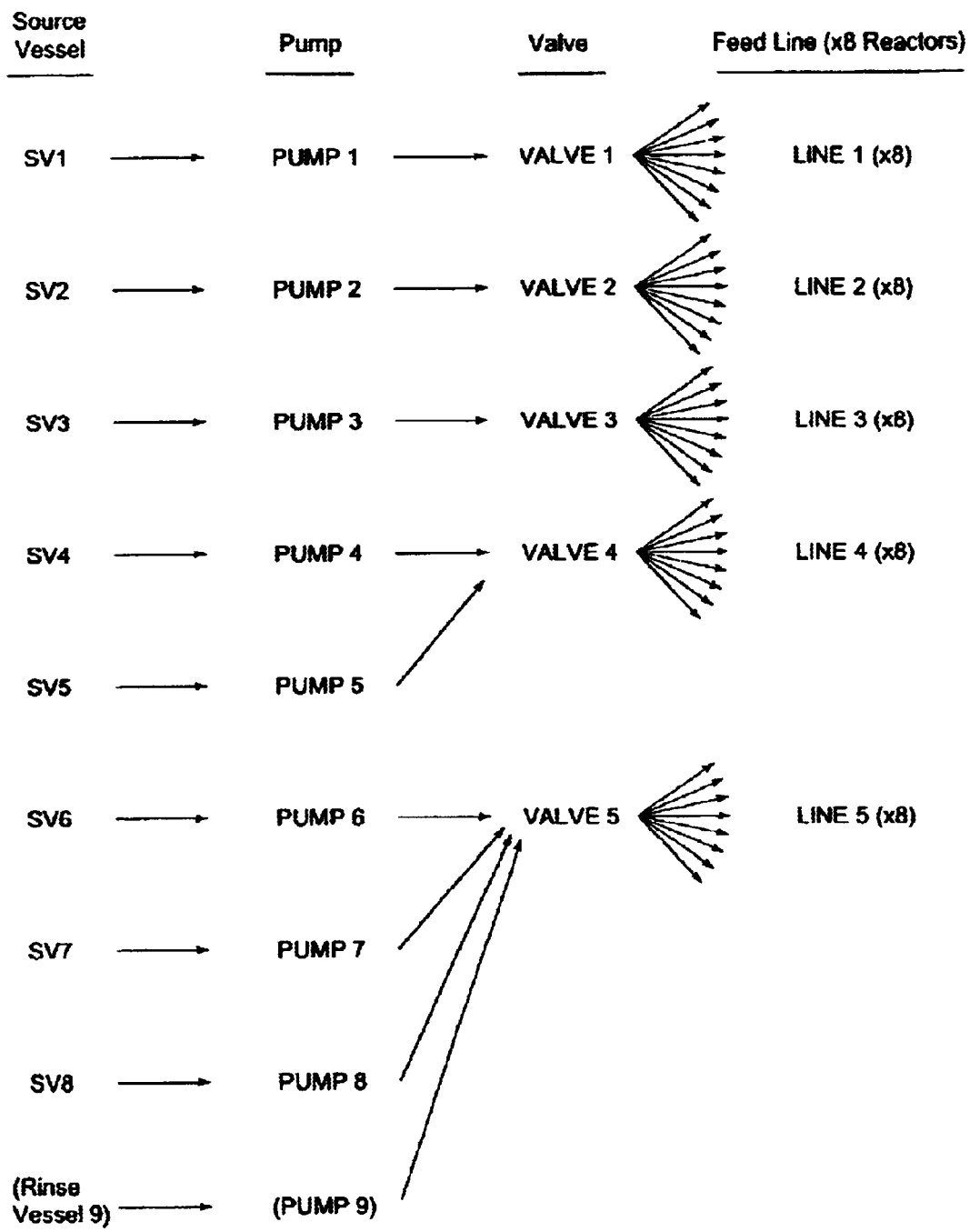
FIG. 2F is a schematic of another embodiment of the feed distribution system of the present invention having dedicated distribution pumps, non-dedicated distribution valves, and dedicated distribution valves.

Another non-limiting, exemplary distribution system can provide reagent distribution from each of eight reagent source vessels (as well as a ninth rinse vessel) to each of eight reaction vessels through eight (or nine) dedicated pumps, five non-dedicated distribution valves, and five non-dedicated feed lines, as follows, with reference to FIG. 2F. A first reagent source vessel (SV1) can be aligned to a first dedicated feed line (LINE 1) for each of the eight reaction vessels through a dedicated first distribution pump (PUMP 1) and a first feed distribution valve (VALVE 1). Likewise, second and third reagent source vessels (SV2, SV3) can be aligned to dedicated second and third feed lines, respectively (LINE 2, LINE 3) for each of the eight reaction vessels through dedicated second and third distribution pumps, respectively (PUMP 2, PUMP 3) and second and third feed distribution valves, respectively (VALVE 2, VALVE 3). A fourth reagent source vessel (SV4) and a fifth reagent source vessel (SV5), can each be aligned to the same common fourth feed line (LINE 4) through separate dedicated fourth and fifth pumps, respectively (PUMP 4, PUMP5), and a common non-dedicated feed distribution valve (VALVE 4). Similarly, each of a sixth, seventh and eighth source vessel, optionally together with a ninth rinse vessel (SV6, SV7, SV8, SV9), can each be aligned to the same common non-dedicated fifth feed line (LINE 5) through separate dedicated sixth, seventh, eighth and ninth pumps, respectively, (PUMP 6, PUMP7, PUMP8, PUMP9), and a common non-dedicated feed distribution valve (VALVE 5). Such a feed distribution scheme strikes a balance between total operational flexibility (since some reagent source vessels share some feed lines) and cost (e.g. especially costs associated with distribution valves).

A further non-limiting, exemplary distribution system can provide completely dedicated reagent distribution from each of eight reagent source vessels (as well as a ninth rinse vessel) to each of eight reaction vessels through eight dedicated distribution pumps, eight dedicated distribution valves, and eight dedicated feed lines, as follows. Briefly, with reference to FIG. 2G, first through eighth reagent source vessels (SV1 through SV8) can be aligned to dedicated first through eighth feed lines, respectively (LINE 1 through LINE 8) for each of the eight reaction vessels through dedicated first through eighth distribution pumps, respectively (PUMP 1 through PUMP 8) and first through eighth dedicated feed distribution valves, respectively (VALVE 1 through VALVE 8). Such a feed distribution scheme is preferred with respect to maximum operational flexibility.

Regardless of the particular distribution system configuration, it may be useful at higher pressures and with certain types of pumps (e.g. syringe pumps) to provide at least one feed-pressurization station pressurizable to a pressure of not less than about 50 psig, with which each of the at least two (or at least three, preferably at least four) liquid feed lines (or at least a portion thereof) can be in selectable fluid communication—such that the feed lines can prefeed the one or more liquid reagents to the feed-pressurization station under pressure to prepressurize the four feed lines (or at least a portion thereof) prior to feeding the one or more liquid reagents to the four or more reaction vessels. The feed-pressurization station can, in especially preferred embodiments, also function as a waste vessel, for collection of waste feed. With reference to FIG. 2E, for example, a feed-pressurization station 1205 is provided with an appropriate pressure-control system. The feed-pressurization station 1205 is in selectable fluid communication with feed line 300 through distribution valve 400 and appropriate conduits and optionally, additional valving. The feed-pressurization station 1205 can be any pressurized zone, but is depicted in FIG. 2E as comprising a liquid space and a gaseous headspace, with pressure in the pressure chamber being maintained at or near the desired system operating pressure. In operation, a reagent in one of the aligned source vessels 100 can be taken up in the pump reservoir during the intake mode of the pumping cycle, and then discharged through feed line 300 and the distribution valve 400, which is selected to the feed-pressurization station 1205, maintained at the desired pressure. Advantageously, prefeeding the one or more liquid reagents to the feed-pressurization station under pressure allows the upstream portion of the feed distribution system (feed line 300) to contain prepressurized liquid reagent feed—thereby minimizing feed-addition errors that would otherwise (i.e., in the absence of such pre-pressurizing) arise due to compressibility of the liquid reagent, and in some cases, due to pressure-induced expansion of the feed line (e.g. when the feed line is a non-rigid, expandable material, such as Teflon or other non-rigid polymers). Such errors could be appreciable in smaller-scale systems and/or where exacting control over total volume of feed addition or feed rates are important for the reaction of interest. Subsequently, the prepressurized liquid reagent feed in feed line 300 can then be fed into one or more of the reactor vessels 500 during the reaction under the reaction conditions through distribution valve 400 (selected to the particular reaction vessel 500) and downstream feed line 300' (such down-stream feed line 300' already being at the reaction pressure, for example, in systems without the check valve shown in feed line 300'). In a preferred operational embodiment, the pressure in the feed-pressurization station 1205 (e.g., pressurized waste vessel) can be substantially the same as the pressure in the reaction vessel 500 to which the feed will be delivered (i.e., at reaction pressure for feed delivered during the reaction under reaction conditions). In other operation embodiments, however, the pressure can be different from the pressure in the associated reaction vessel 500, and still provide for at least some of the aforementioned benefits. In some configurations, there may be two or more, three or more or four or more pressurization stations (e.g., corresponding to the number of feed pumps, or to the number of distribution valves or to the number of reactors).

Additionally, and regardless of the particular distribution system configuration, it may also be useful at higher pressures and with certain types of pumps (e.g. syringe pumps) to provide a pressure chamber to absorb and attenuate fluctuations in pressure in the system that are associated with pump start-ups, pump-mode shifts (e.g., from intake mode to output mode) or other pressure-pertubation-causing events. With reference to FIG. 2E, for example, a pressure chamber 1200 can be provided with appropriate valving and conduits to provide fluid communication with each of the reaction vessels 500. The pressure chamber 1200 can comprise a liquid space and a gaseous headspace, with pressure in the pressure chamber being maintained at or near the desired system operating pressure.

As discussed in greater detail below, in addition to the three or more liquid feed lines, each of the two or more (preferably four or more) reaction vessels can comprise one or more gas ports providing fluid communication between the reaction vessel and one or more external requirements, such as one or more gaseous sources (e.g., for feeding gaseous reactants to the reaction vessel, for purging the reaction vessel with an inert gas, and/or for controlling reaction pressure), or one or more pressure sensors for monitoring and/or controlling reaction pressure. Gaseous delivery can be effected by conventional means known in the art. For operating at higher pressures (e.g., at pressures equal to or greater than the pre-pressure of gaseous reactant tanks as commercially available), it may be advantageous to include pressure-boosting equipment within the fluid distribution system. With reference to FIG. 2E, for example, a pre-pressurizer 1210 (operating roughly analogous to an accumulator) can be used to prepressurize a reactant gas (e.g. loaded from a gas source vessel 1220 at lower pressures into a first gas space 1211 on a first side of a piston 1212) using an inert gas available at higher pressures (e.g. and loaded at higher pressures into a second gas space 1213 on a second side of a piston 1212).

The pumps employed in the present parallel reactor system are preferably positive displacement pumps, and are preferably adapted for small volume increments. Pump control, and step size are important further considerations. Exemplary pumps include syringe pumps, and other pumps generally disclosed in the aforementioned related patent applications. Digitally-controlled syringe pumps are particularly well suited to the present invention, and can add the desired volume using from about 3000 to about 12,000 increments of the total volume.

Discharge Distribution System

The discharge distribution system for any of the aforementioned semicontinuous embodiments or continuous embodiments can provide fluid communication between the reaction vessel and a waste reservoir, a sampling system (e.g., for characterization of a sample taken from the reaction mixture, and/or another reaction system (e.g. for feed to a second reaction vessel in a series). As shown in FIGS. 2A through 2D, for example, the discharge distribution system can comprise a discharge valve 700 or sampling valve (also 700) that provides selective fluid communication between the discharge line 600 and one of a waste collection system, a sample analysis system, a second reaction system, and/or another system. Although shown in FIGS. 2A through 2D with only a single discharge line 600, each reaction vessel 500 could alternatively have two or more discharge lines (for sampling and/or waste).

It is also contemplated that a feed distribution line could also be used as a discharge line (e.g., by reversing the direction of the pump). In one embodiment, for example, one or more of the 8 liquid feed systems can be run in "reverse" to sample aliquots of the reaction mixture from each vessel, for reaction monitoring or off-line analysis. In this case it may be especially desirable to have additional valves connected to the distribution manifold to allow for sample collection, flushing or washing of the syringe, lines, or valves, or expelling excess reagent to a waste-collection vessel. It may also be desirable to connect one or more input lines supplying each syringe to either a distribution valve to select multiple reagent feeds to one distribution channel, or to an XYZ robotic probe that can select multiple sources. Similarly, the output lines from one or more of the valves may be connected to a distribution valve or to an XYZ robotic probe to enable delivery of aliquots sampled from the reactor vessels to different sample containers.

Reaction Vessels

The reaction vessels are preferably chemically inert. A reaction vessel can be formed in a material that provides structural support (e.g. stainless steel) or can be a vial or liner within another structure. Various general configurations for the reaction vessels are described in the aforementioned related U.S. patent applications and are expressly incorporated herein by reference. The reaction vessel is preferably a research reactor vessel, but could also be a relatively small-volume production vessel.

In a preferred embodiment, two or more (preferably four or more) reaction vessels are provided in a reactor block. The reactor block can include two or more (preferably four or more) reaction cavities, each having an interior surface that defines or contains a reaction vessel. Hence, the two or more (or four or more) reaction vessels can be wells formed in the reactor block, or alternatively, can be removable liners supported by wells formed in the reactor block. Such liners have an interior surface defining a cavity for containing a liquid reaction mixture, and an external surface dimensioned so that the liner fits within the wells.

Referring to FIGS. 4A through 4H, a reactor block 520 can comprise a base block 530 and a header block 540. A reaction vessel 500 of the present, invention can comprise an inner surface 505 at least partially formed in the base block 530. The inner surface 505 can additionally, or alternatively define at least a portion of a reaction cavity or, equivalently, a reaction chamber 510, that forms the pressure boundary around each reaction vessel, when considered with appropriate seals, etc. The reaction cavity 510 can contain a reaction vessel 500 (FIG. 4G) such as a removable liner (e.g. glass vial). The inner surface 505 can be formed in the base block 530 as two or more (or four or more) wells 532 (FIG. 4G) that define or contain the reaction vessels 500, or as through-holes 534 (FIG. 4B) with associated bottom plate 533. The header block 540 can be removably positioned (e.g., secured through non-permanent fasteners such as bolts or latches, not shown) over the base block 530 such that it provides access to the reaction vessels 500 (when removed) and such that it forms two or more (preferably four or more) pressurizable reaction cavities or chambers 510 (when secured in position). One or more seals, such as individual o-ring type seals 535 can be positioned between the base block 530 and the header block 540 in grooves 536 formed in the base block 530 and/or the header block 540 to individually seal each of the two or more (preferably four or more) reaction cavities or chambers 510. The pressurized reaction chambers or cavities 510 can include or be defined, at least in part, by the interior surface 505 of the base block that defines or contains the reaction vessel. The reaction cavities or chambers 510, and in turn, the reaction vessels 500 in fluid communication therewith (e.g., sharing a common headspace therewith) can be pressurized to the operating pressures values discussed below. Further details regarding the reactor block 520, including preferred sealing configurations, and rupture protection configurations, are described in the aforementioned related, co-pending, co-owned patent applications U.S. Ser. No. 09/177,179, U.S. Ser. No. 09/211,982, U.S. Ser. No. 09/548,848, and in PCT patent application WO 00/09255, each of which are hereby specifically incorporated by reference.

In a particularly preferred embodiment, with further reference to FIGS. 4A through 4D, the reaction vessel 500 can further comprise at least 3 feed ports 515 in fluid communication with the reaction chamber 510, and at least 3 independent feed lines 300 providing fluid communication between the at least three feed ports 515 and at least three corresponding, dedicated or non-dedicated reagent source vessels (e.g, through pumps, and other components of a distribution system, as described). Each of the three or more feed lines has a distal end 305 in fluid communication with the reaction chamber of the reaction vessel. The distal end 305 of the feed lines 300 can terminate, for example, at one or more of the following positions: at the at least three feed ports 515; at a position internal to the reaction cavity 510 (whether above or below the reaction vessel 500 (e.g. especially where the reaction vessel is a removable reaction vessel 500 that shares a common headspace with the reaction cavity 510 pressure boundary); or at a position internal to the reaction vessel 500. The distal end of the three or more feed lines can, in one embodiment, define an opening (e.g., circular opening) through which the reactant fluid can pass to enter the reaction zone of the reaction vessel. The feed lines and/or reaction vessel configuration is preferably designed to minimize dead volume within the reaction vessel.

Figure 4E:
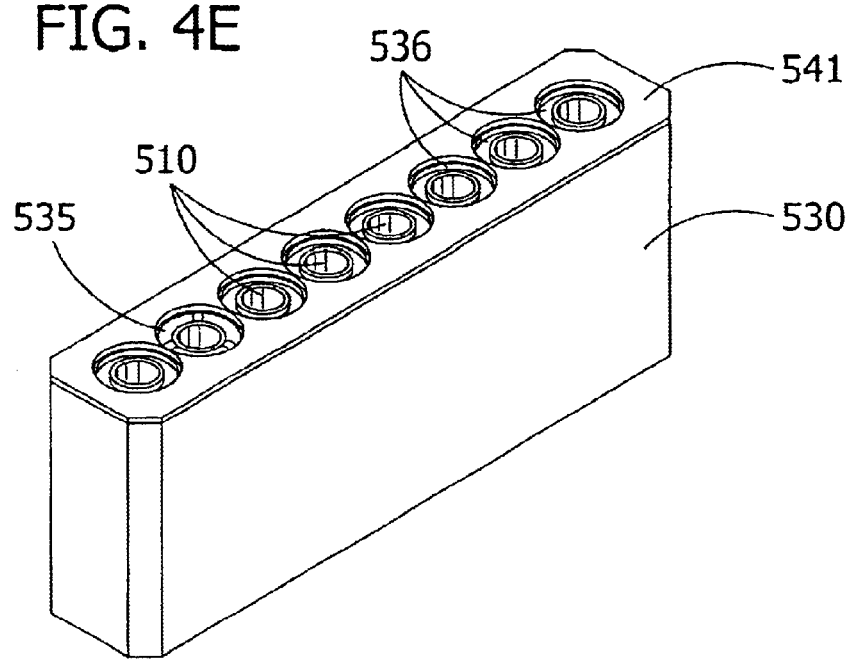
FIG. 4E is a perspective of a base block of the present invention.
Figure 4F:
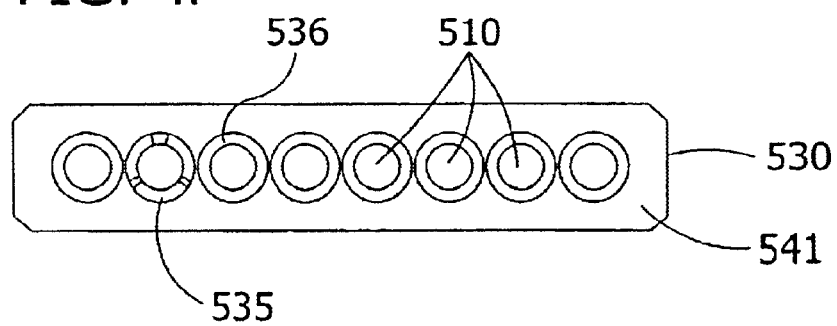
FIG. 4F is a top plan view of the base block of FIG. 4E.
Figure 4G:
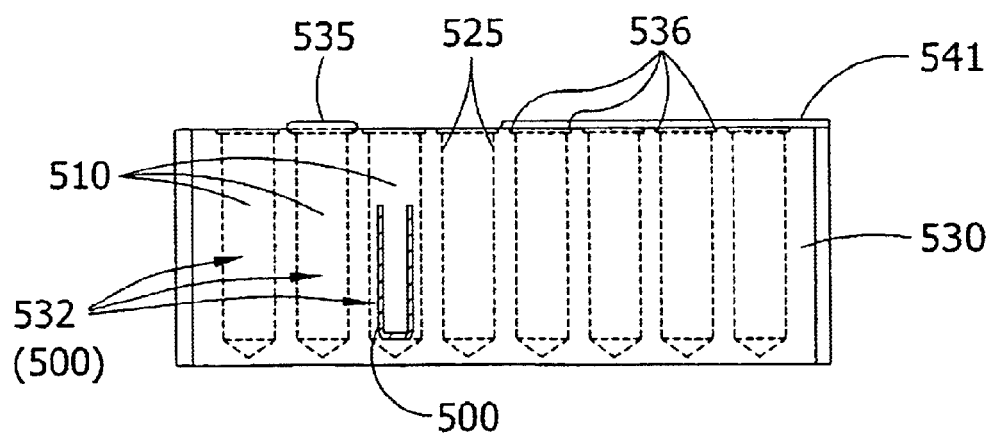
FIG. 4G is an elevation of the base block of FIG. 4E.
Figure 4H:
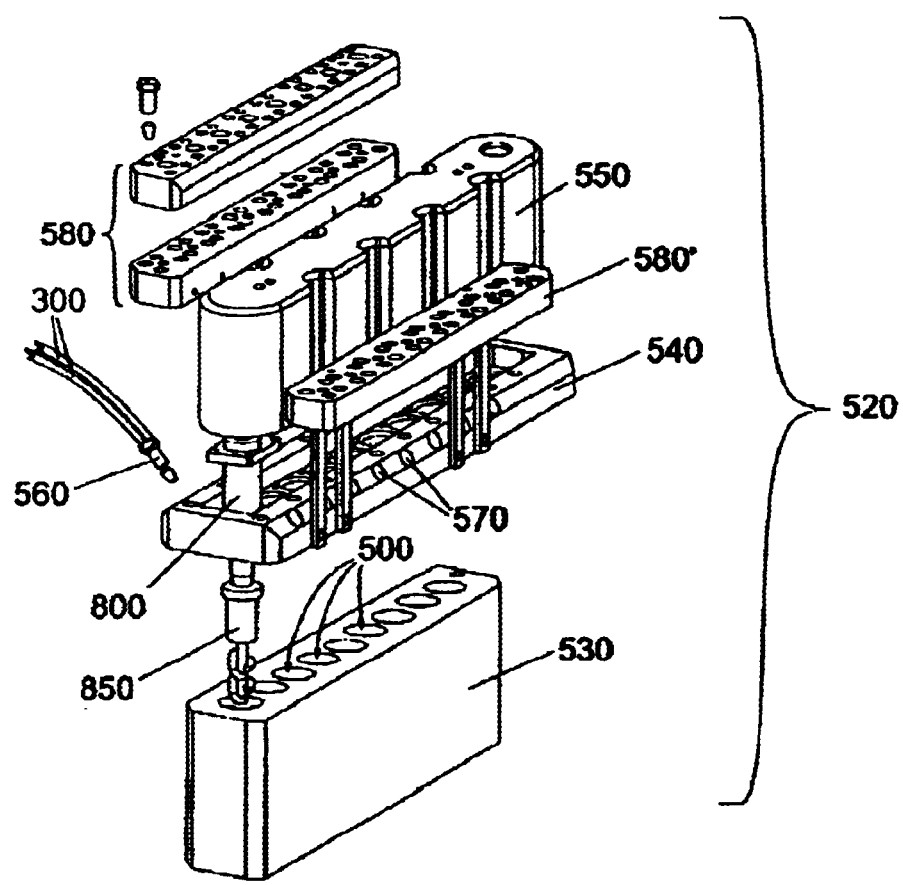
FIG. 4H is an exploded perspective of the reactor block of the present invention.

In the preferred embodiment, in which the reaction vessels are provided in a reactor block comprising a base block 530 and a header block 540 with reaction cavities 510 formed in the base block and/or the header block, the reactor block can further comprise one or more header gaskets 541 situated between the header block and the base block (FIGS. 4E, 4F, and partially in 4G). The header gasket(s) 541 can serve as seals (as discussed above), and can additionally or alternatively also be adapted to mask the portion(s) of the header block 540 that are exposed to the reaction cavity (cavities) 510. Specifically, a header gasket 541 can be a unitary, disposable header gasket having two or more, preferably four or more masking regions that correspond (in number, and in shape) to the reaction cavities 510 (i.e., to the exposed portions of the header block 540 within the reaction cavities).

The reaction vessels can be a semi-continuous (i.e., semi-batch) reaction vessels having the multiple feed lines, but without a continuous discharge line. The semi-continuous vessels can have a discharge line for intermittent sampling, however. If desired (e.g., for a continuous flow embodiment), the reaction vessel 500 can likewise be a continuous reaction vessel, and can comprise at least one discharge line having a distal end in fluid communication with the reaction chamber of the reaction vessel. In either case, the feed distribution system can be a multiplexed system comprising the selection valves dedicated to each feed channel, as described above.

Figure 5B:
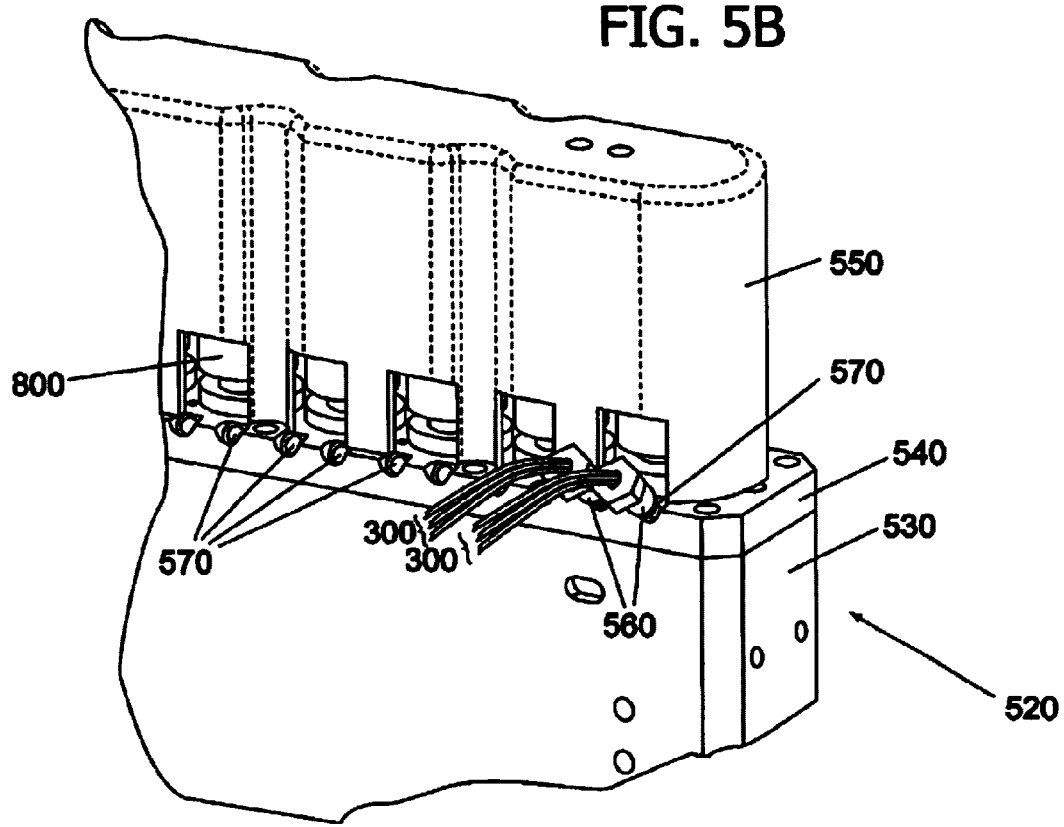
FIG. 5B is an enlarged, fragmentary perspective of an assembled reactor block of the present invention.
Figure 5C:
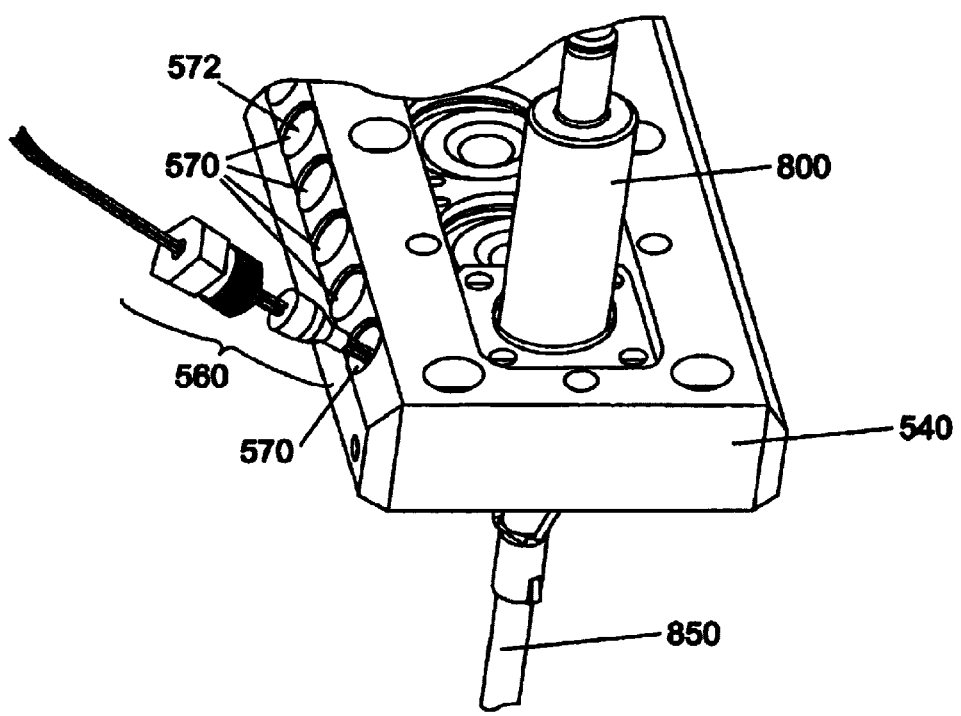
FIG. 5C is an enlarged, fragmentary perspective of a header block of the present invention.

Each of the reaction vessels can preferably comprise one or more gas ports 522 (FIG. 4B) providing fluid communication to the reaction cavity 510 (and inherently to the reaction vessels 500) and serving, for example, as gaseous feed ports, pressure-monitoring ports, pressure control ports, or gaseous purge ports. Preferably each of the reaction vessels comprises a pair of gas ports 522. Independent pressure control for each of the n reaction vessels is particularly important in connection with the semicontinuous and continuous parallel reactor embodiments disclosed herein. Dedicated independent pressure control systems can maintain a constant system pressure during addition of additional feed volumes (gas or liquid), during discharge of a portion of the reaction mixture, to account for changes in pressure effected by the reaction itself (e.g., the formation of gas-phase products during the course of the reactions), and/or to account for differences in temperature between different reaction vessels. Pressure control is preferably under the control of a microprocessor, with set-points established based on the reactions and reaction conditions of interest. As shown in FIG. 4B, each of the reaction vessels 500 can also include a pressure relief system, shown generally at 531. Briefly, the pressure relief system can include a relief passageway 531a, a rupture disk 531b (e.g., commercially available from Parr), and an expansion volume 531c, which can for example be an outlet flow path leading to waste collection The geometry of the reaction vessel or the reaction cavity or chamber is not, by itself, particularly critical. The reaction vessels can be open or closed, but if open, are preferably contained within a closed reaction chamber or reaction cavity that can be pressurized, substantially as described herein and in the aforementioned related patent applications. The reaction vessels can generally be substantially of the same (e.g. cylindrical) volume as compared between reaction vessels, or can be of different volume. Each of the reaction vessels can have a substantially uniform (e.g., circular or oval) cross section (as taken radially). In some embodiments, however, the reaction vessel can have a varying, non-uniform cross section, combining for example both an oval cross section (as taken radially) in a first (e.g., upper) portion of the reaction vessel and a circular cross section (as taken radially) in a second (e.g., lower) portion. With reference to FIG. 5A, for example, having an oval cross section (or equivalent thereof) in an upper portion 511 of the reaction cavity 510/reaction vessel 500 can advantageously allow for additional space on at least one side, and preferably on both sides of a shaft-driven stirring mechanism, through which multiple feed lines can be provided. In particular, in a preferred or particularly preferred embodiment, each of the two or more, preferably four or more, reaction vessels are defined by or contained in a lower portion of a reaction cavity having a first size and/or shape (e.g., circular shape). The upper portion of the reaction cavity can have a second size (e.g, with a larger cross section) and/or shape (e.g. oval shape) taken radially, relative to the size and/or shape of the lower section, such that there is additional space for passing the feed lines through the upper section to the lower section of the reaction cavity.

In one preferred embodiment, the reaction vessel can be a substantially right-cylindrical volume and can have an aspect ratio (L/D) of at least about 1.0, preferably about 1.5, and more preferably at least about 2, and in some embodiments at least about 2.5 or at least about 3.0.

The reaction vessel preferably has a volume ranging from about 1 ml to about 1 liter (l), preferably from about 1 ml to about 500 ml, and more preferably from about 1 ml to about 100 ml, still more preferably from about 2 ml to about 50 ml, yet more preferably from about 2 ml to about 25 ml, and most preferably from about 5 ml to about 15 ml. The smaller size of the reactor allows for a decrease in the waste stream per reaction conducted. However, such a small scale still allows for generation of enough material (e.g., in a polymerization experiment, for example, resulting in about 1–5 grams of dry polymer) to do a variety of scientifically meaningful rapid and/or conventional characterizations techniques. Small-volume reaction vessels also have a larger surface-to-volume ratio (S/N) than conventionally-sized "bench-scale" vessels, and as such, can efficiently and effectively explore investigations of parameter spaces involving heat transfer or other properties for which the S/V ratio is important. The volume of each of the two or more, preferably four or more reaction vessels is preferably the same between different reaction cavities, but can alternatively, vary between cavities to investigate the effect of reaction vessel volume. In some applications, each of the various embodiments of the invention can be advantageously applied with reaction vessels having larger reaction volumes, including for example, reaction volumes of up to about 2 liters, up to about 4 liters and/or 10 liters, or more.

Each of the reaction vessels can be pressurizable to and/or operated at pressures required for the chemistry of interest. In preferred embodiments, the reaction pressures or design pressure for the reactor can be at atmospheric pressure, or at pressures greater than atmospheric pressure, preferably at least about 15 psig, more preferably at least 50 psig, 100 psig, yet more preferably at least about 200 psig, still more preferably at least about 400 psig, and in some embodiments, at least about 500 psig, at least about 700 psig, or at least about 1000 psig, and in some instances, at least about 1200 psig. Preferred pressure ranges include from about atmospheric pressure to about 3000 psig, preferably from about 100 psig to about 2500 psig, more preferably from about 200 psig to about 2000 psig, and yet more preferably from about 400 psig to about 1500 psig. In some embodiments, the pressures can range from about 500 psig to about 1200 psig, from about 500 psig to about 1500 psig, or from about 1000 psig to about 1500 psig. Such pressures and pressure ranges can be particularly applied in connection with non-biological polymer research applications. In some applications, the reactor is preferably hermetically sealed.

Temperature control of the reaction vessels can be effected substantially as described in the aforementioned related, co-pending, co-owned patent applications U.S. Ser. No. 09/177,179, U.S. Ser. No. 09/211,982, U.S. Ser. No. 09/548,848, and in PCT patent application WO 00/09255, each of which are hereby specifically incorporated by reference. In general, temperature control can be individual with respect to each reaction vessel, or modular with respect to two or more, preferably four or more reaction vessels. In preferred embodiments, a reactor block can comprise or be in thermal communication with one or more temperature control elements (e.g., resistive heaters, thermoelectric heaters, fluid-based heat exchangers, etc.) for individual or modular temperature control. Operating temperatures can typically range from about 25 C to about 300 C, preferably from about 100 C to about 200 C for many applications, and if cold-temperature applications are required, preferably from about –100 C to about 300 C.

Stirrers

The reaction vessels are preferably mechanically stirred, and in particular, are preferably stirred with a shaft-driven stirrer (e.g., shaft-driven impeller) stirring mechanism. The shaft-driven stirrer (e.g., impeller) can be advantageous over other types of stirring approaches, such as magnetic bar stirrers, mixing balls w/rockers, shaking, etc., due to higher stirring power and to the controllable variability in mixing profile achievable through a combination of varying stirrer geometry and impeller speed for each of the parallel reactors. The shaft-driven stirrer (e.g., impeller) can be driven directly from a motor, or indirectly via magnetic coupling. Preferred shaft-driven stirring embodiments are disclosed in the aforementioned related patent applications, including, for example, U.S. Ser. No. 09/548,848 filed Apr. 13, 2000 by Turner et al, entitled "Parallel Reactor with Internal Sensing and Method of Using Same". The particular geometry of the shaft-driven stirrer (e.g., impeller) is not narrowly critical, and can vary depending on the type of mixing desired for a particular reaction of interest For many reactions, it is desirable to employ a shaft-driven stirrer (e.g., impeller) having a geometry that provides for substantial axial and substantial radial mixing (the axial direction being considered to be substantially parallel to the axis of the shaft of the impeller). A number of generally preferred, exemplary shaft-driven stirrer (e.g., impeller) geometries are shown in FIGS. 3A through 3F. With respect to the auger-type shaft-driven stirrer (e.g., impeller) depicted in FIG. 3C, the number of turns per inch, and the pitch can be adjusted as desired to achieve a desired mixing profile. Moreover, the pitch can be fixed or variable, and can be controllably varied throughout the course of the reaction. In operation, it may be desirable to change impeller speed (and where possible, other variables) to account for changes in fluid viscosity within the reaction vessels during the course of the reactions. It may also be desirable to have different impeller geometries in the stirrers for each of two or more different reaction vessels, such that differences in mixing profiles can be investigated in parallel reactions.

With further reference to the figures, the reaction vessels 500 in these preferred and particularly preferred embodiments can further comprise a shaft-driven impeller stirrer (850, FIGS. 2A through 2D and 3A through 3E, not shown in FIGS. 4A through 4D), and preferably having a magnetically-coupled drive motor 800. The drive motor 800 can alternatively be directly coupled to the shaft/impeller 850. The shaft-driven stirrer 850 can be mounted on, and comprised in the header block 540 of the reactor block 520, as shown in FIGS. 4A through 4D, and in FIG. 4H, with the header block 520/stirrer 850 subassembly positioned over the base block 530 to provide a sealed, pressurizable, reaction chamber 510 (once mounted and positioned). A cover 550 (FIG. 4H) can cover the two or more drive motors 800, in a sealing or non-sealing manner, as appropriate for the operating environment.

Figure 3A:
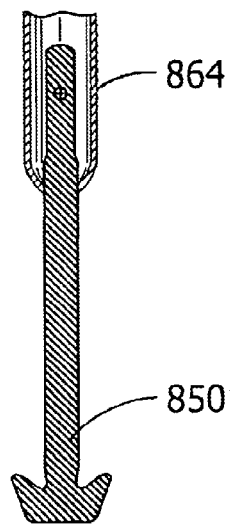
FIG. 3A is an elevation of one embodiment of an exemplary shaft-driven stirrer.
Figure 3B:
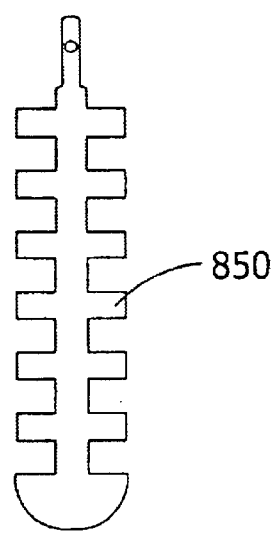
FIG. 3B is an elevation of another embodiment of an exemplary shaft-driven stirrer.
Figure 3C:
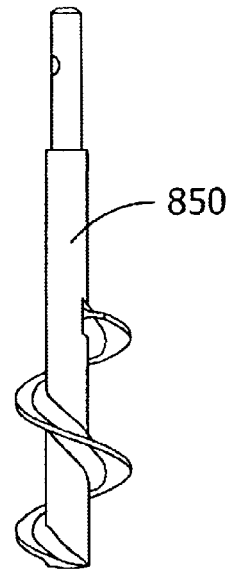
FIG. 3C is an elevation of yet another embodiment of an exemplary shaft-driven stirrer.
Figure 3D:
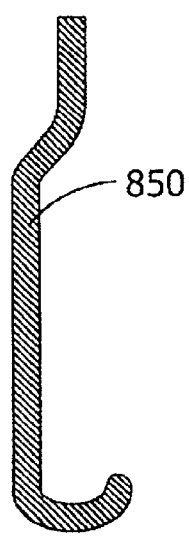
FIG. 3D is an elevation of still another embodiment of an exemplary shaft-driven stirrer.
Figure 3E:
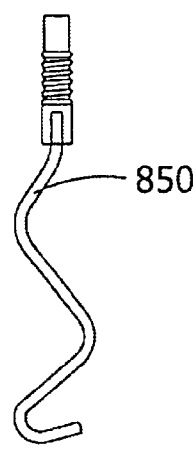
FIG. 3E is an elevation of yet another embodiment of an exemplary shaft-driven stirrer.
Figure 3F:
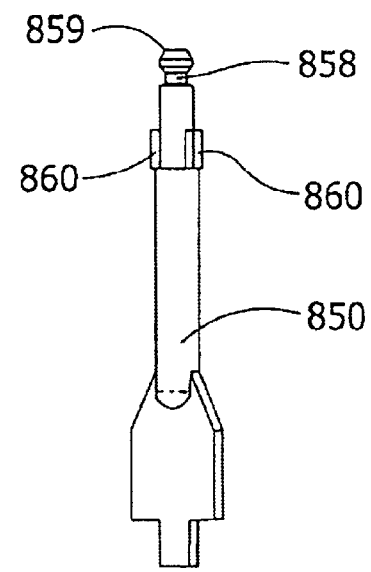
FIG. 3F is an elevation of a further embodiment of an exemplary shaft-driven stirrer.
Figure 3G:
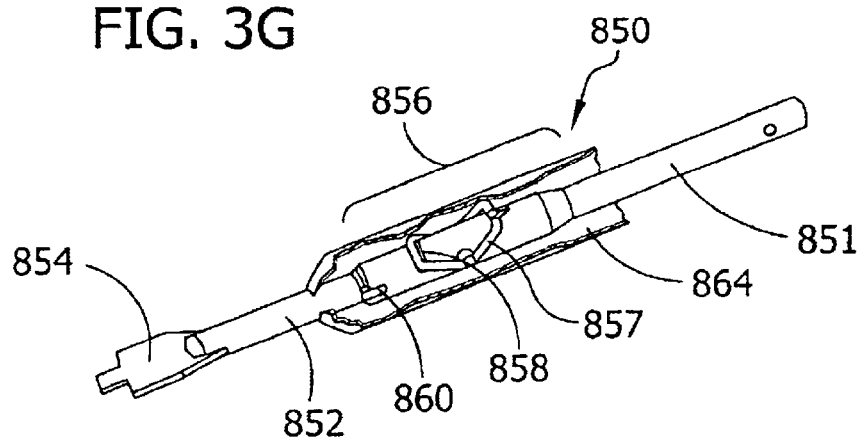
FIG. 3G is a perspective of the shaft-driven stirrer of FIG. 3F illustrating one embodiment of a latching mechanism of the stirrer.
Figure 3H:
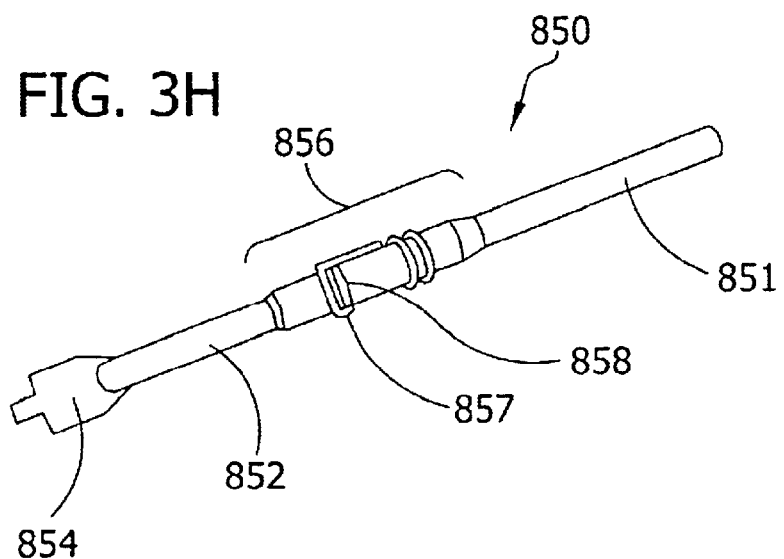
FIG. 3H is a perspective of the shaft-driven stirrer of FIG. 3F illustrating the latching mechanism of FIG. 3G.
Figure 3I:
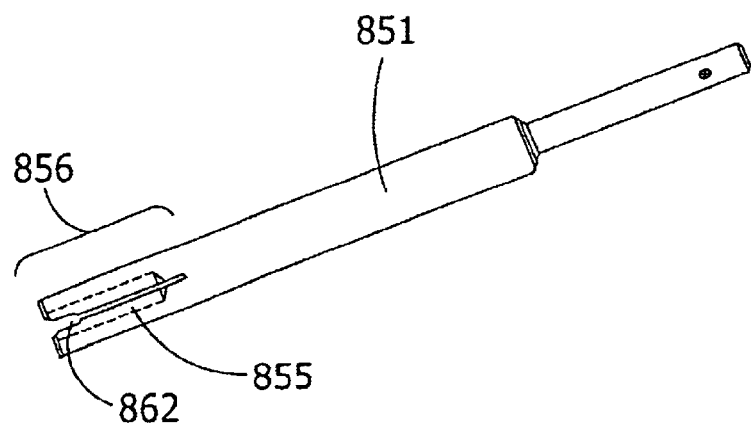
FIG. 3I is a perspective of the shaft-driven stirrer of FIG. 3F illustrating another embodiment of the latching mechanism of the stirrer.

The shaft-driven impeller stirrer 850 can be a unitary shaft that is directly coupled to the drive motor 800. Alternatively, with reference to FIGS. 3F through 3I, the shaft-driven stirrer can be a two-piece shaft comprising a first upper shaft 851 engageable with the drive motor 800 and a second lower shaft 852 having the stirring element 854. The first upper shaft 851 and the second lower shaft 852 can be detachably connected from each other (e.g., for cleaning and/or disposal/replacement) through a latching mechanism, generally referred to in FIGS. 3G and 3H as 856. A latching mechanism 856 comprises a latch spring 857 secured to the first upper shaft 851, that can releasably engage a circumferential indent 858 near the upper end 859 (FIG. 3F) of the second lower shaft 852. With reference to FIG. 3I, an alternative, spring-less latching mechanism 856 can be a pressure-fitted connection, in which the upper portion of a second lower shaft 852 (e.g., such as that shown in FIG. 3F—not shown in FIG. 3I) can be pressure-fitted into a slotted aperture 855 of a first upper shaft 851. In either of the aforementioned embodiments, a drive mechanism, such as a combination of a drive key 860 on the second lower shaft 852 and a lock 862 on the first upper shaft 861 (or vice versa) can be employed with the latch mechanism 856. Advantageously, the second lower shaft 852 of the two-piece shaft 850 can be disposable, as indicated above.

As an alternative to, or in addition to a disposable shaft (e.g., a disposable second lower shaft 852), the stirring system can, for each shaft-driven impeller, also comprise one or more shaft covers 864 adapted to mask at least a non-disposable portion of the shaft-driven impeller. Specifically, with reference to FIGS. 3A and 3G, shaft covers 864 can mask the entire shaft 850 (including the impeller portion), or a portion thereof—such as masking a first, non-disposable upper shaft 851 of a two-piece shaft 850, where the second lower shaft 852 is a disposable shaft. Use of such disposable shaft covers 864 facilitates clean-up after the reaction of interest.

Feed Lines—General

The number of independent feed lines (e.g., liquid reagent feed lines) in each reaction vessel can be at least two feed lines, but for these preferred and particularly preferred embodiments is preferably at least 3, more preferably at least 4, more preferably at least 8, and in other embodiments, can be integer numbers up to about 10 or more (e.g, at least 12 or at least 16), or in some cases up to about 20, and in general, can range from about 4 to about N (as defined above) and preferably from about 4 to about 20 or from about 4 to about 10.

The feed lines 300 and discharge line(s) 600 can be of any suitable size, but preferably have an inside diameter (e.g., orifice size) ranging from about 10 $\mu$m to about 1 mm, preferably from about 50 $\mu$m to about 500 $\mu$m, and most preferably from about 100 $\mu$m to about 250 $\mu$m. Smaller orifice size, especially when applied in combination controllable valve switching, and finely-controlled pumps, is particularly advantageous over prior art systems due to the fine volume control achievable when adding additional reagents during the course of the several reactions. In particular, the at least two, preferably at least three, more preferably at least four feed lines have an inside diameter of not more than about 1 mm. In some embodiments, the outside diameter is not more than about 1 mm, and the inside diameter is not more than about 700 μm.

The feed lines may be made of any material or combination of materials. Portions of the feed lines in contact with the reaction environment should preferably be compatible with the chemistry of interest. The feed lines can generally be of any spatially suitable geometry (e.g., circular, square, rectangular, etc. in cross-sectional shape). In general, feed lines may be provided as capillaries, channels (e.g., micromachined channels—typically having a diameter of less than about 1 mm, and preferably of less than about 100 μm), tubing, etc. The feed lines can be rigid feed lines, or non-rigid feed lines under reaction-pressure conditions. The feed line material may include, for example, glass (e.g., fused silica), polymers (e.g., PTFE (Teflon), polyethylene, PEEK) or metals or alloys (e.g., stainless steel)—or any other material suitable for the chemistry (for the portion in contact with the reaction environment), suitable for the pressure and flow conditions of the reaction system, and if necessary, suitable for use with various connectors, etc. Although shown in the various figures as being capillaries and/or flexible tubing, it is likewise envisioned that other suitable conduits, such as micromachined channels could be employed as part of the feed and/or discharge distribution system.

In some embodiments, at least a portion of the feed lines can be integral with (e.g., machined (including micromachined) into) the reactor block (e.g. into the header block and/or the base block). Various other components of the feed-distribution system (e.g. valving) and/or of a sampling system could likewise be integral with the reactor block. Some specific embodiments of integral feed distribution are disclosed in related, co-owned U.S. patent application Ser. No. 09/826,606 entitled "Parallel Reactor for Sampling and Conducting In-Situ Flow Through Reactions and a Method of Using Same", filed Apr. 5, 2001 by Chandler et al., which is hereby incorporated by reference in its entirety for all purposes.

Varying Feed Line Size

In some embodiments, the reaction vessels comprise at least two, at least three feed lines, or preferably at least four feed lines, and one or more of the at least three feed lines (or at least four feed lines), or a first subset thereof, have a different inside diameter (e.g., orifice size) or cross-sectional area relative to the one or more other of the at least three feed lines, or a second subset thereof. Variable diameter or cross-sectional area of the feed/discharge lines offers a further control variable for actively controlling the overall volume and rate of feed addition to each of the reaction vessels. It is also typically desirable to have small-diameter tubing as the feed line into each reaction vessel, so that small drops are delivered more "evenly" (i.e., temporally more continuous) to the reaction, and so that the reagent being added has a short contact time with heated surfaces before being introduced into the reaction mixture. The combination of smaller and larger sizes is also indicated in connection with this aspect of the invention. Since small-diameter tubing limits flow rates, it may be desirable to have larger diameter tubing for reagents delivered in larger volume (such as solvent) or at faster feed rates, and smaller diameter tubing for reagents delivered in smaller volume (such as catalysts and initiators) or at slower feed rates. As a non-limiting example, the inside diameter for one or more of the feed lines can be less than about 500 μm while another of the feed lines going to the same reaction vessel can be about 500 μm or more.

Feed-Line Grouping/Modular Feed-Line Subassemblies (e.g., Ferrules)

The feed lines can be grouped for service to each of the two or more, preferably four or more reaction vessels. With reference to FIG. 5A, for example, guide brackets 542 can be mounted on a header block 540 of the reactor block 520 to guide at least three, preferably at least four feed lines 300 into the reactor block 520—entering either through the header block 540 (as shown) or alternatively through the base block 530 (not shown).

Moreover, the at least two, at least three, or preferably at least four feed lines can enter the reactor block individually, as shown for example in FIGS. 4A through 4F, and in FIG. 5A, and can be sealed using epoxies or other sealants (not shown), or using individually mounted mechanical fittings (e.g., individual swage-lock type fittings, not shown) mounted in the feed ports 515 of the reactor block 520. Alternatively, and advantageously, the at least three, preferably at least four feed lines can enter into the reactor block in modular fashion as a bundled collective group. Preferably, the modular group of feed lines can be removably attached—preferably efficiently connected and/or disconnected to and/or from the reactor block through a modular feed-line subassembly. Specifically, the at least three, preferably at least four feed lines can be provided to the reactor block (and ultimately to one or more reaction vessels) through one or more modular feed-line subassemblies. In some embodiments, higher numbers of feed lines can be accommodated through each of the feed-line subassemblies—including for example at least six feed lines, preferably at least eight feed lines, at least twelve feed lines, at least sixteen feed lines or at least twenty-four lines. Each of the feed-line subassemblies is adapted to releasable engage the reactor block and to support at least two, preferably at least three, more preferably at least four feed lines passing into the reaction cavity or reaction vessel.

Figure 5D:
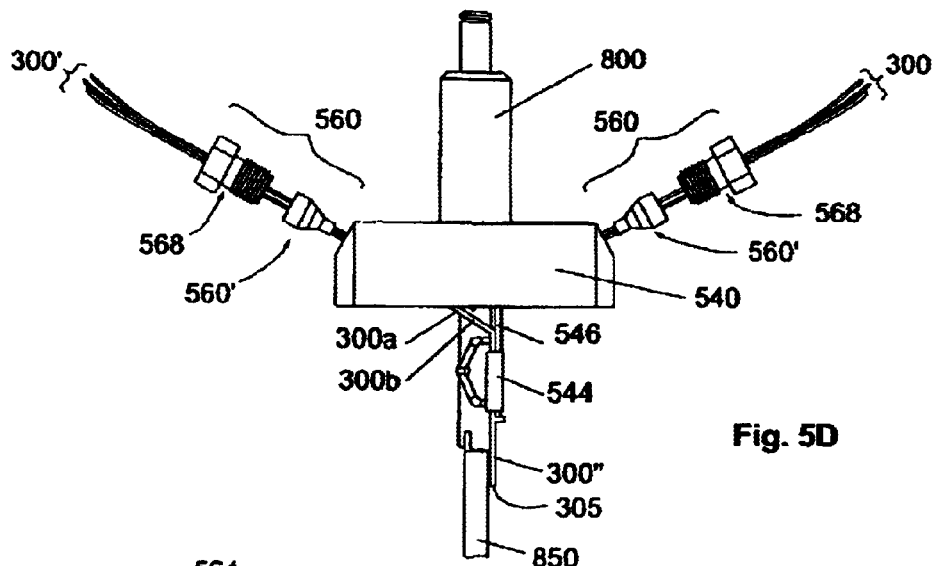
FIG. 5D is an end elevation of a header block illustrating one embodiment of modular feed-line subassemblies.
Figure 5E:
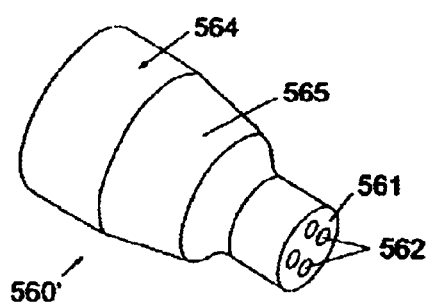
FIG. 5E is an enlarged perspective of one embodiment of a ferrule of the present invention.
Figure 5F:
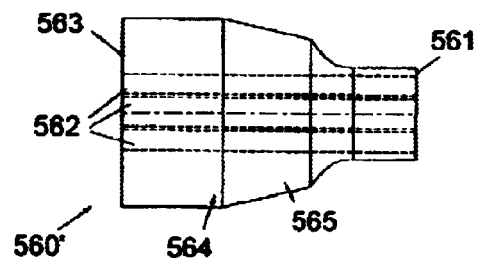
FIG. 5F is a side elevation of the ferrule of FIG. 5E.
Figure 5G:
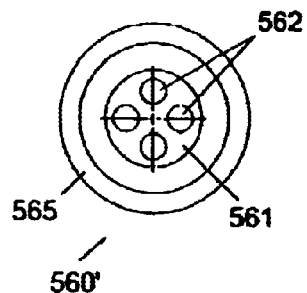
FIG. 5G is an end elevation of the ferrule of FIG. 5E.
Figure 5H:
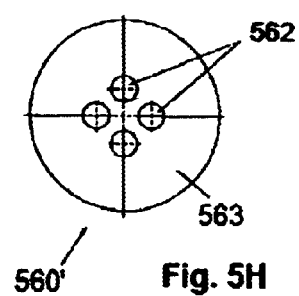
FIG. 5H is an opposite end elevation of the ferrule of FIG. 5E.

The particular design of the feed-line subassemblies is not narrowly critical. In one exemplary embodiment, a feed-line entrance bracket having at least two, preferably at least three, more preferably at least four individual mechanical fittings (e.g. swage-lock type fittings) mounted on a common bracket can be employed as the feed-line subassembly. In a preferred embodiment, with reference to FIG. 4H and FIGS. 5B through 5H, the modular feed-line subassembly can be a ferrule 560 (referenced as shown without a fastener in FIGS. 5D through 5H by reference numeral 560'). The ferrule 560 (560') comprises two or more apertures 562 adapted to support, and preferably to sealingly support the at least two feed lines 300 when the ferrule 560 is engaged with the regetor block 520 (e.g., with header block 540). Regardless of the particular configuration for the modular feed-line subassembly, the subassembly is preferably engaged either with the header block 540 (as shown) or alternatively with the base block 530 of the reactor block 520. In a preferred embodiment, the header block 540 or the base block 530 can comprise four or more feed-line subassembly receiving ports 570. Each of the receiving ports 570 is in fluid communication with the reaction cavity 510 (and with the reaction vessel 500) and is adapted to receive one of the ferrules 560, and preferably to releasably and to sealangly sealingly engage one of the ferrules 560. With reference to FIGS. 5E through 5H, each of the one or more ferrules 560' comprises a first interior end 561 for insertion into the corresponding receiving port 570 in the reactor block 520, a second exterior end 563 substantially opposing the first interior end 561, two or more, preferably four or more internal apertures 562 extending from the first interior end 561 to the second exterior end 563 for supporting the at least four liquid feed lines 300 passing into one of the reaction vessels 500. The ferrules 560' further comprise an external side surface 564 including a tapered portion 565, the tapered portion 565 having a smaller cross-section at positions closer to the first interior end 561 relative to positions farther from the first interior end 561, the tapered portion 565 being configured to correspond to a tapered surface 572 defining a portion of the receiving port 570. The ferrule 560' also comprises a fastener 568 for releasably engaging at least the tapered portion 565 of the ferrule 560 (560') with the corresponding tapered surface 572 of the receiving port 570. The fastener 568 can be, for example, a hollow threaded nut that engages corresponding threads on the receiving port 570. The ferrule 560' can be of a compressible material such that when engaged, the tapered portion 565 of the ferrule 560' seals with the corresponding tapered surface 572 of the receiving port 570, and each of the at least two apertures 562 seals the corresponding at least two feed lines 300. In any case, as shown in FIG. 5D, preferably two or more modular feed-line subassemblies 560 can provide feed lines 300 to the same reaction cavity 510/reaction vessel 500. The two or more feed-line subassemblies 560 can be orientated on the same side or different (e.g., opposing) sides of the reactor block (e.g., header block).

Additionally, regardless of the particular design, the feed-line subassemblies (e.g. ferrules) can further comprise one or more apertures adapted to support, and preferably sealing support one or more instrumentation lines, including for example, lines for thermocouples, pressure-sensors, pH sensors, in-situ analysis (e.g., fiber-optic probes), etc.

Distal-End Position

In the preferred or particularly preferred embodiment (and in other embodiments having at least two, preferably at least three, more preferably at least four feed lines 300 for a reaction vessel or for each of two or more, preferably four or more reaction vessels 500) the distal end 305 of each of the feed lines 300 can be positioned to substantially the same depth in the reaction cavity 510 or reaction vessel 500 (as shown in FIG. 4B). Alternatively, although not shown in the figures, the distal end 305 of one or more of the feed lines 300, preferably some first subset of the total number of feed lines 300, can be positioned lower in the reaction cavity 510 or reaction vessel 500 as compared to the distal end of one or more other feed lines, preferably some other second subset of the total number of feed lines. In particular, if a liquid-phase reaction is being run with a gaseous headspace, the distal end 305 of the feed lines 300 can be positioned to terminate in the gas phase (shorter extension into reaction chamber 510) or in the liquid phase (longer extension into the reaction chamber 510). It may be particularly advantageous for some such applications to have at least some of the feed lines terminating in the gas phase, and at least some of the feed lines terminating in the liquid phase (i.e., directly into the liquid reaction mixture). Without being bound by theory not specifically recited in the claims, differences in the surface tension associated with the interface defined between the distal end 305 of the feed lines 300 and the gas phase (the gas interface) as compared to the surface tension associated with the interface defined between the distal end 305 of the feed lines 300 and the liquid phase (the liquid interface), can result in differences in feed delivery, and provide a greater degree and/or different nature of feed control. That is, feeding through the gas interface can result in temporally intermittent feeding profile due to the formation of drops at the distal end 305 of the feed lines 300, whereas feeding through the liquid interface can result in a substantially temporally continuous feeding profile (assuming substantial phase compatibility between liquid feed and the liquid reaction mixture). In any case, the at least two, preferably at least three, and more preferably at least four feed lines can be supported in the reaction cavity 310 by one or more guide posts 544 (FIG. 5D). The guide post 544 can be supported by the head block 540 through guide-post bolt 546.

Detachable, Multi-Section Feed Lines/Parallel Feed-Line Interface

In the preferred and particularly preferred embodiments and in other embodiments having at least two, preferably at least three, more preferably at least four feed lines 300 for a reaction vessel or for each of two or more, preferably four or more reaction vessels 500), the feed lines 300 can comprise at least a first section and a second section in fluid communication with each other. Advantageously, the second section can be detachably connected from/releasably engaged with the first section at a feed-line junction, thereby allowing a second section contaminated from the reaction, for example (i.e., having a distal end in the reaction mixture or in the reaction vessel in proximity to the reaction mixture), to be detached, cleaned or disposed, and replaced with the cleaned or new second section.

The first and second sections of the feed line can be detachably connected (releasably engaged) from each other by an suitable approach, including for example individual mechanical connectors (e.g., union couplers), or thermal heat-shrinking. In a preferred approach with reference to FIGS. 4H and 6A, a parallel feed-line interface 580 can provide for fluid communication between a first section 300*a* and a second section 300*b* of each of at least four liquid feed lines 300. The feed-line interface 580 can comprise a modular first source-side piece 581 and a modular second reactor-side piece 582 that are releasably engageable (e.g., through a bolted connection) with each other to provide the fluid communication between the first and second sections 300*a*, 300*b* of the feed line 300. Additionally or alternatively, the interface 580 can be releasably connected to the first section 300*a* (e.g., through heat shrink of the first section 300*a* onto annular nodules 584 of the first source-side piece 581, as shown in FIG. 6A) and additionally or alternatively, to the second section 300*b* (e.g., through mechanical connectors 586, of each of the at least four liquid feed lines). As shown, the interface 580, 580' can be mounted on or otherwise supported by the reactor block, but could alternatively (or additionally for additional interfaces 580, 580') be separate from the reactor block (e.g., used for multiple connections elsewhere in the feed distribution system, such as by the one or more distribution valves 400).

The junction point between the first and second section 300*a*, 300*b* of feed lines 300 can be external to the reaction cavity (e.g. as shown in FIG. 6A, with parallel interface 580 connection), or can be internal to the reaction cavity (e.g. as shown in FIG. 5D, with individual heat-shrink connection). More particularly in one embodiment, the first section 300*a* is positioned entirely outside of the reaction cavity 510, or at least partially outside of the reaction cavity 510, preferably at least outside of the reaction vessel 500—such that it is substantially uncontaminated by the liquid reaction mixture (i.e., can be used again, preferably without or with only nominal cleaning effort). Hence, at least a portion of the first section 300*a* can be inside the reaction cavity 510.

The feed line 300 can additionally comprise a third section 300*c* or higher numbers of sections, each in fluid communication with each other, and detachably connected as described above, individually or in modular fashion—for example with the interface 580. Moreover, different types of feed line materials can be employed with respect to each section, depending on the desired attributes for that section of the feed line. In a preferred exemplary, non-limiting approach, the feed line can include a first section 300*a* of polymer-coated (e.g. polyimide-coated) fused silica detachably connected (e.g., by heat-shrink) to a second section 300*b* of PEEK or Teflon, substantially as shown in FIG. 5D. The first section 300*a* can, in turn, be detachably connected to a third section 300*c* of the feed line 300, the third section 300*c* being Teflon or PEEK. In another exemplary, non-limiting embodiment, a Teflon or PEEK tubing first section 300a can be detachably connected to a stainless steel tubing second section 300b (e.g., by mechanical connection), as shown in FIG. 6A.

Multiple Modules

The reaction vessels can be independent of each other, or can be combined in a single module, as disclosed in FIGS. 4A through 4H, FIGS. 5A through 5C and FIG. 6A. Banks of modules can be combined to form a parallel reaction vessel have large numbers of reaction vessels.

The entire reactor system may be placed in an inert atmosphere or controlled atmosphere chamber (such as a glovebox).

Use/Operation

The reactor is useful for polymerization reactions as well as for a broader range of organic or inorganic reaction processes where it is desirable to have feed additions during the course of the reaction—for example, to control exothermicity, to maintain relatively small, steady-state concentrations of reactants, or to effect different staged phases of a multistep reaction. The apparatus also has applications involving chemical processes that do not necessarily involve a chemical reaction—such formulations, blending, or crystallization processes. Although preferably designed for high-pressure applications, the apparatus and features disclosed herein can also be used at relative low pressures, including atmospheric pressure. In lower pressure applications, the apparatus is preferably (but not necessarily) at least hermetically sealed.

Many reactions (or interactions that do not necessarily involve the making and/or breaking of chemical bonds, such as blending, formulations, crystallization) require the slow addition of one or more components to a reaction over time- The presently-described reactor can be equipped with the appropriate tubing and valving to add a defined amount of a reactant chemical to any selected reactor well, over a defined period of time (within the constraints of the reactor volume, pump precision and the maximum flow rate controlled by pump speed, tube diameter and chemical viscosity). Multiple components are often important as there may be several stages to a reaction which each may require several different chemicals to be added (initiators, monomers, boosters, quenching reagents, etc.). The added reagents may generally be gas and/or liquid, depending on the reaction of interest Such multi-feed protocols are particularly advantageous with polymerization reactions such as emulsion polymerizations. In this area, for example, it is desirable to add several monomers, water, surfactant solution, initiators, and redox reagents all in a concerted, time-controlled manner, in multiple stages during the course of a reaction.

The extent, order and temporal profile (e.g., rate) of feed additions can be carefully controlled using the present invention, as can the rate and/or order of discharges. In particular, the control system can include control of the pumps, control of the switching valves, pressure controllers, all integrated. In general, the control is flexible, and advantageously, it can be coordinated with library design software (e.g., "Library Studio™", Symyx Technologies, Inc., Santa Clara, Calif.) and/or synthesis control software (e.g., "Impressionist™", Symyx Technologies, Inc., Santa Clara, Calif.), such as is disclosed in the aforementioned related patent applications. One advantageous application of the described system is that sensitive reagents may be manipulated in pumps in lines on a benchtop or in a simple hood, so that blanketing the entire reactor system in inert atmosphere may not be necessary, even for sensitive chemistry. In fact, one or more distribution channels may be used for gas distribution, either to flush the reactors with inert atmosphere before beginning a reaction, or for introduction of metered amounts of gaseous reagents.

Reaction protocols that can be advantageously effected with the parallel reactor of the invention can generally be categorized into three temporal phases—initial reaction charge ("IRC") as a $1^{st}$ phase, slow additions of one or more reagents ("slow adds") as a second phase, and finish or mop-up ("finish") as a third phase.

In the initial reaction charge phase, the system is sealed, and typically purged with inert gas. Some set of starting reagents may be added to the reaction vessels via external means prior to closure and purging, or using the distribution and feed system described either prior to or after closure and purging. The reaction vessels are then heated to the desired (initial) temperatures (each cell may have a different temperature) while at the same time stirring each initial mixture with an shaft-driven stirring paddle. Typically, feed control is less significant, albeit still important, in the initial charge stage In the second, slow-add phase, a number of reagents (e.g. eight reagents) are fed to the reaction vessels, preferably independently of each other, using the distribution and feed system described. Exemplary slow additions for polymerizations include monomer additions, initiator trickle, surfactant trickle, make-up solvent, etc. Significantly, the system has the capabilities to control the total volume of each of the reagents being fed to each reactor, the sequence (relative order) of each feed addition, and temporal profile (e.g., feed rate, temporally incremental vs. temporally continuous, number of increments, size of increments (e.g., volume or time of increments), etc.) of each feed addition. Feed control is particularly important in connection with this second, slow-add phase. The particular nature and/or degree of feed control capabilities will depend on the arrangement of the feed distribution system. For example, in reactor systems having eight dedicated feed lines feeding eight reagents to each of eight reaction vessels (e.g., through a distribution system that includes feeding each of the eight reagents from its source vessels through its dedicated pump and its dedicated feed distribution valve), addition volumes can be carefully and efficiently controlled—since each feed path is dedicated between one reagent and one of the eight reactors. In contrast, in reactor systems having some non-dedicated feed paths (e.g. by feeding eight reagents through three dedicated feed lines and two non-dedicated feed lines to each of eight reaction vessels), addition volumes for the non-dedicated (i.e., shared) feed lines may be less carefully (e.g., some mixing of reagents allowed, volume of the feed tubes and/or uniformity of feed tubes affect the dispensed volume) and/or less efficiently (e.g., some intermittent rinsing steps required) controlled. Hence, dedicated systems as described in connection with FIG. 2G are preferred with respect to efficiency and control. Other feed control aspects described above can also be incorporated into a particular system. Generally, it is most advantageous (in terms of dispensing precision and flexibility) for each feed distribution channel to be dedicated to one homogeneous liquid reagent solution. However, it is also possible to dispense heterogeneous mixtures, including mixtures of immiscible liquids and slurries of solids, within the metering precision, pump design and chemical compatibility constraints imposed by the specific chemistry.

In the third, finish phase, reagents can be added for various purposes, such as to stop (e.g., quench) the reaction, to consume left-over reactant, or to impart useful properties to the resulting product mixture (e.g., stabilizers, anti-microbial agents, etc.).

Regardless of the particular phase of the reaction, several feed strategies can be effected for feeding multiple reagents to each of the multiple reactors. The following feed strategies can be effectively employed for various configurations of the feed distribution system For example, in systems where each of eight feed lines to each of eight reaction vessels has its own source vessel (i.e. sixty-four source vessels in total) with straight-line feeding from each of the source vessels through dedicated pumps directly to the reaction vessel (without a distribution valve), complete operational flexibility is retained with respect to feed strategy. That is, reagent 1 (R1) can be simultaneously fed to any or each of the eight reaction vessels, serially or simultaneously with any or each of the other reagents. Substantial operational flexibility can also be achieved—with significant simplification and savings in cost—using systems where each of the eight feed lines to each of the eight reaction vessels has only one source vessel, but with a dedicated feed distribution system as described above in connection with FIG. 2G. Regardless of the particular configuration, the parallel reactor/multi-feed system of the invention can generally be operated and controlled continuously and in parallel (simultaneously) with respect to each reaction vessel. However, because chemical reactions typically occur over longer periods of time, strategies involving staggered, serial control over the reactions can be effected without substantially affecting the reaction performance, for many operations of interest.

According to one such staggered control strategy, reactor feed control is effected for each reaction vessel on a rotating serial basis—considering and providing the feed requirements for the first reaction vessel, then the second reaction vessel, then the third reaction vessel, etc., and continuing serially until each of the reaction vessels have been controlled during this first round of control. Control attention is then rotated back to the first vessel, to further consider and provide the feed requirements thereto, and then sequentially through the second reaction vessel, etc. until each of the reaction vessels have been controlled during the second round of control. The sequential control strategy is then repeated until each of the reactions have been completed. Such sequential control strategy can be effected from a "per reactor" (i.e., "per reaction-vessel") framework—with a single overall control system focusing control attention on all of the feed requirements for a particular reaction at that time, and controlling all of the feed streams to meet those requirements at that time. Alternatively, control can be effected from a "per reagent" (or "per feed line") framework, with multiple independent control systems. Here, each feed line is independently controlled on a staggered basis—that is, independent of the control of other feed lines, with delays or passes (no control effected), as appropriate, to allow for required sequence order of different reagents. Regardless of the control framework, each control event associated with a particular reactor can include, for example, determining the feed requirements for that stage of the reaction—typically by reference to a pre-programed recipe of feed versus time of reaction, but optionally including some real-time or near-real-time feedback loop, with the feed being adjusted to meet a predetermined setpoint (e.g., feeding for pH control, or temperature control). Various feeds can then be added to the reaction vessel to satisfy the then-current feed requirements, for example, by operating the pumps (e.g., syringe pumps), by opening valves in a particular feed line at an appropriate time to select the appropriate receiving vessel and align it to the proper feed in the proper order, by injecting the required fraction of the total amount of that reagent to be added, and then by closing that valve and opening the next one. Rapidly cycling through the valves in each line—under either framework—allows for pseudo-continuous addition of reagents.

More specifically, chemical reactions can be effected in a parallel, semi-continuous or continuous reactor, preferably a pressure reactor pressurizable to not less than about 50 psig. The reactor can comprise four or more semi-continuous or continuous reaction vessels, four or more liquid reagent source vessels, and at least four liquid feed lines providing selectable fluid communication between the four or more liquid reagent source vessels and the four or more reaction vessels, as follows. The volume of the reaction vessels is preferably less than 1 liter. A chemical reaction is initiated in each of the four or more reaction vessels under reaction conditions that can include a reaction pressure of not less than about 50 psig. The chemical reaction can be sequentially initiated in each of the four or more reaction vessels, or alternatively, it can be initiated in each of the four or more reaction vessels at substantially the same time. The four or more liquid reagents are fed into the four or more reaction vessels during the reaction under the reaction conditions, while controlling, for each reaction vessel, a total volume of each of the liquid reagents being fed to the reaction vessel during the reaction, a number of stages in which the total volume for each of the liquid reagents are fed to the reaction vessel during the reaction, a stage volume defined by a percentage of the total volume associated with each of the stages for each of the liquid reagents, and a feed sequence defined by a relative order in which the stages for each of the liquid reagents are fed to the reaction vessel during the reaction. The total volume can be the same or different as compared between different reagents. The number of stages can be the same or different as compared between different reagents, and can be one or more stages, and is preferably at least 2 stages, more preferably at least four stages, and in some cases, more preferably at least ten, at least one hundred stages or higher numbers. The number of stages can typically range from about 1 to about 1000, preferably from about 1 to about 100, and more preferably from about 2 to about 20. The stage volume can also be the same or different as compared between different stages for each of the liquid reagents. The feed sequence can include, with respect to a particular reaction vessel, sequential feeds of various different reagents, or simultaneous (coinciding or overlapping) feeds of various different reagents to that reaction vessel. The total volume, number of stages, stage volumes and feed sequence can be selected with consideration to the involved chemistries.

Preferably, control is also effected over a temporal profile associated with feed addition to the reaction vessel for each of the stages for each of the liquid reagents. The temporal profile for each stage can be defined by a number of feed increments in which the stage volume is added to the reaction vessel, and the period of time in which the stage volume is added to the reaction vessel. Each feed increment represents a separate, discrete addition of a reagent to the reaction mixture in the reaction vessel. With syringe-type pumps, for example, each feed increment can correspond to an individual pump operation. The number of feed increments can be the same or different as compared between each of the stages, and between each of the reagents, and can generally be one or more increments. A single feed increment represents a temporally continuous feed over the period of feeding the stage volume. The number of feed increments for each stage can, in some embodiments, be at least two increments, at least four increments, and in some cases, at least ten increments, at least one hundred increments or higher numbers. The number of increments can typically range from about 1 to about 1000, preferably from about 1 to about 100, and more preferably from about 2 to about 20. The duration or period over which the stage volume is added to the reaction vessel can be, equivalently, expressed as a start time for adding each stage volume and a stop time for adding each stage volumes. The increment volumes (e.g., defined as a percentage of the stage volumes) can also be controlled, and can be the same or different as compared between different increments of a stage. Likewise, in some embodiments, with some types of pumps, the actual delivery flowrate can be controlled for each feed increment added to the reaction vessel.

The feed control systems can include one or more microprocessors for controlling the operation of the various pumps, distribution valves, etc., substantially as described. The control system can also include one or more clocks or other timing devices for controlling the feed sequence of the various stages for the various reagents, and within each stage, for controlling the incremental feed additions. A single master clock can be used alone, and/or in conjunction with additional clocks, such as additional subservient clocks. In one embodiment, each reaction vessel can have its' own associated clock, alone, or in conjunction with a master clock. In an supplemental or alternative embodiment, each feed line (or feed pump) can have its' own associated clock. The control clocks can also be used in connection with controlling other reaction parameters (pressure, temperature, etc), in addition to feed control.

In preferred embodiments, feed control is effected sequentially, on a rotating basis (e.g., rotating through each of the four or more reactors, or through some subset thereof), for each of the four or more reaction vessels during the reaction. More specifically, such sequential control is effected by (i) considering and providing the feed requirements for a first reaction vessel at a first time after initiation of the chemical reaction therein, and thereafter, (ii) by considering and providing the feed requirements for a second reaction vessel at a second time after initiation of the chemical reaction therein, and thereafter, (iii) by considering and providing the feed requirements for a third reaction vessel at a third time after initiation of the chemical reaction therein, and thereafter, (iv) by considering and providing the feed requirements for a fourth reaction vessel at a fourth time after initiation of the chemical reaction therein. Thereafter, such sequential control is continued by (v) reconsidering and providing additional feed requirements for the first reaction vessel at a fifth time after initiation of the chemical reaction therein, the fifth time being a time later than the first time, and thereafter, (vi) by reconsidering and providing additional feed requirements for the second reaction vessel at a sixth time after initiation of the chemical reaction therein, the sixth time being a time later than the second time, and thereafter, (vii) by reconsidering and providing additional feed requirements for the third reaction vessel at a seventh time after initiation of the chemical reaction therein, the seventh time being a time later than the third time, and thereafter, (iv) by reconsidering and providing additional feed requirements for the fourth reaction vessel at a eighth time after initiation of the chemical reaction therein, the eighth time being a time later than the fourth time. In one operational variation, the chemical reaction can be sequentially initiated in each of the four or more reaction vessels such that the time elapsed between reaction initiation and the first, second, third and fourth times at which the feed requirements arc considered and provided for the first, second, third and fourth reaction vessels, respectively, are substantially the same as compared between reaction vessels.

Several different triggering events can be employed in such staggered control strategies for advancing the sequence of control from one reaction vessel to the next in the series. For example, the advance of control can be based solely on regular, recurring time intervals—where control attention is paid to each reaction vessel in turn for a set period of time (e.g., two minutes), with the feed requirements updated to the extent possible during that set period of time, and then advanced to the next reaction vessel. In an alternative approach, the advance of control can be task-oriented, rather than being based solely on preestablished time intervals. In such a task-oriented approach, advance of control occurs only after the feed requirements for the controlled reaction have been completely updated for the reaction occurring therein. That is, control attention is paid to a first reaction vessel and the feed requirements for that reaction vessel are adjusted until fully updated (i.e., the actual feed inputs are matched with the preset feed requirements, for that moment in time). Thereafter, control can advance to the next reaction vessels, and so on in serial staggered fashion The task-oriented approach for advancing control offers substantial advantage over a strict temporal approach, since it gives the user greater flexibility in pre-programming the control scheme or control plan for the reactions. In short, the time required to effect a particular feed change is not arbitrarily limited by the requirement to advance control to the next reaction vessel.

In a preferred approach, feed control is effected under software or firmware control, with a graphical user interface (GUI) for a reactor operator to input feed requirements and/or track the reaction progress in each reactor. According to a preferred approach, the software is programmed to effect a staggered feed control, from a reactor framework, with the control event being triggered on a task-oriented basis, based on predefined user input feed requirements, on real-time or near-real-time feed back control, or combinations thereof.

Figure 7A:
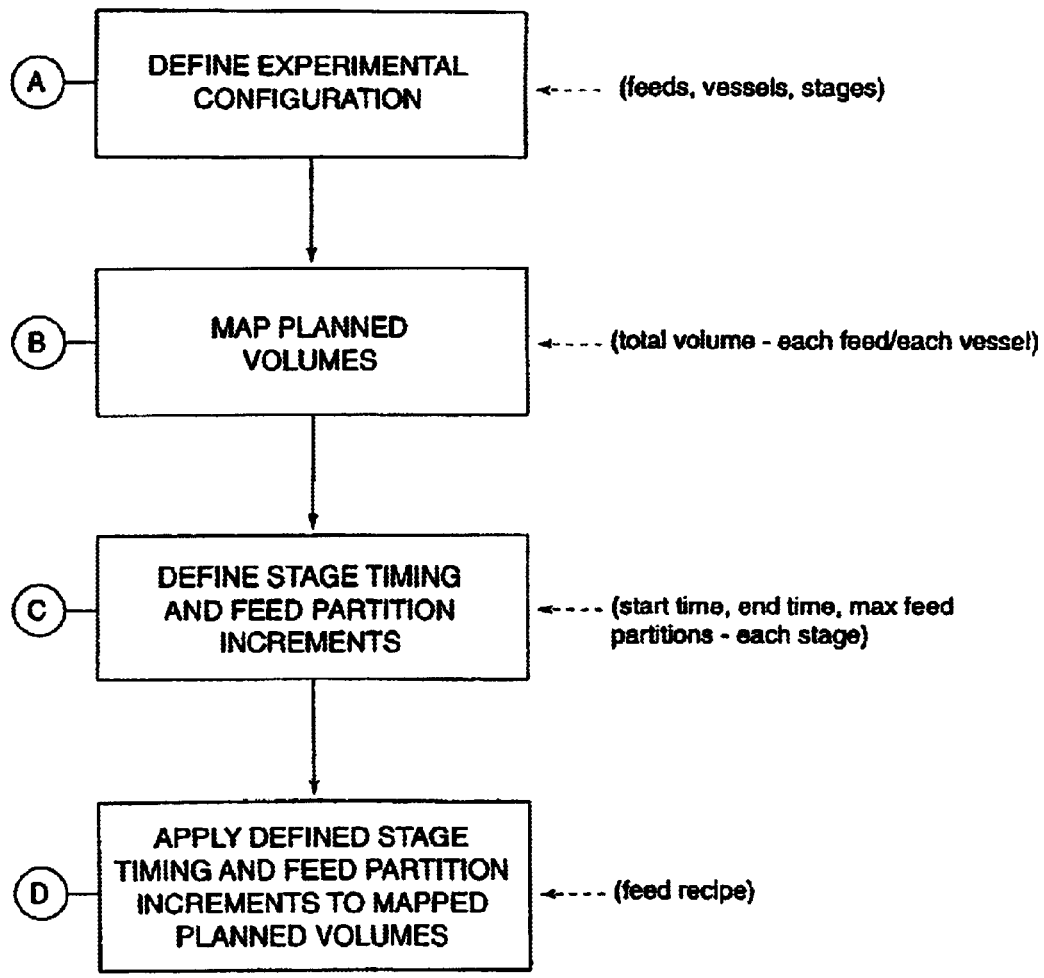
FIG. 7A is a schematic illustrating one embodiment of a process of the present invention.

Preferably, a user can define a detailed feed plan (feed recipe) for the course of reaction associated with each of the two or more, preferably four or more reaction vessels. As noted, such feed recipes can generally include specification of the total volume of each of the reagents being fed to each reactor, the number of stages, the stage volume, the sequence (relative order) of each feed addition (e.g., of each of the stages), and temporal feed profile (e.g., feed rate, temporally incremental vs. temporally continuous, number of feed increments, size of feed increments, etc.) for each feed addition (e.g., for each of the stages). In one approach, particularly suited to a feed distribution configuration similar to that described in connection with FIG. 2G, an experimental set-up can be established as follows. With reference to FIG. 7, the broad experimental parameters, total number of dedicated feed channels, the total number of reaction vessels, and the total number of feed stages are specified (e.g., an experiment using two feeds to each of four vessels, with feed delivery in five stages). (Step A, FIG. 7A). Then, the planned total volume for each feed for each vessel is mapped out (e.g. in a grid). (Step B, FIG. 7A). These preceding steps can be performed using, for example, Library Studio™ (Symyx Technologies, Santa Clara, Calif.). For each stage, a stage volume, a stage starting time, a stage ending time (collectively defining a feed period for that stage) and maximum number of feed partitions or feed increments is defined by the user. (Step C, FIG. 7A). The maximum number of feed partitions or feed increments determines the minimum volume per dispensing event for that stage. Each "mapping" of one reagent to one vessel may be dispensed as one single dispense at any given time, or may be broken into two or more dispenses over any arbitrary length of time. Typically, as noted above, to achieve "pseudo semi-continuous" feeding, a mapping will be divided into about 10 to 1000 dispenses, depending on the dispensing precision of the pump system, and the "smoothness" of addition required by the chemical system. Multiple mappings can, in some embodiments, be dispensed simultaneously. Also, it may be desirable to design the overall final composition of an experiment or library, and then conduct multiple experiments with a given composition differing only in the timing, "smoothness" of addition, temperature control over time, stirring rate, and order of addition of reagents. In any case, the defined stage timing and feed partition increments are overlaid (i.e., applied) onto the mapped plan volume, to define the detailed feed plan (find recipe). (Step D, FIG. 7A).

The system can then be operated to implement the recipe during the course of the reaction, in a staggered feed control, with a reactor framework (controlling feed additions to each reactor at a time), and with the control event being triggered on a task-oriented basis (finishing one task before sequencing to the next reaction vessel. The data from the recipe file is loaded into the control software, and a check is done for errors in recipe plan values. A data structure is then created in software to implement the loaded recipe plan data, and to thereby run the experiment. Once the reaction clock is started (can be user defined or effected), the software sequences through each vessel in series, and determines whether a feed requirement exists for that reaction vessel based on the current time and the associated recipe plan for that feed for that vessel for that time. If a feed requirement exists, that feed is dispense into the reaction vessel. Like determinations and if necessary, dispensing (feeding) events are effected for each of the feeds for that vessel for that time. Once the feed requirements have been updated for that reaction vessel, the software sequences to the next reaction vessel included in the experimental setup, and proceeds in a similar manner. Such operations continue until the experiment is complete. Once the experiment has been completed, the software writes a log-file and/or report to document the actual feeding during the experiment.

The following examples illustrate the principles and advantages of the invention.

Example 1

A parallel semi-batch reactor having eight reaction vessels was configured as follows: an array of eight sealed stainless steel reactor chambers, each equipped with speed-controlled rotary shaft stirrer paddles, disposable glass liner reaction vessels with volume capacity of about 12 ml, argon gas manifold inlet and outlet, thermostatically controlled heating, and five inlet lines into each of the eight reactor vessels, supplied by five pump and valve distribution systems of the invention. The feed lines of each distribution system were primed with the corresponding five liquid reagent solutions described below. The reactor was assembled in a clean, empty state, and sealed. The reactor was pressurized 5 times with argon to a pressure of 60 psig, followed by venting to flush air from the system, and then was maintained under an ambient (1 atm) argon atmosphere during the course of the reaction.

| Feed Number | Label | Composition |
|---|---|---|
| 1 | Monomer mix | butyl acrylate, 86.5% methyl methacrylate, 9.5% acrylic acid, 3.0% hydroxypropyl acrylate, 1.0% |
| 2 | Styrene | styrene, 100% |
| 3 | Water | water, 100% |

-continued

| Feed Number | Label | Composition |
|---|---|---|
| 4 | Surfactant | Rhodacal A246L (Na alpha olefin sulfonate) 10.0% water, 90.0% |
| 5 | Initiator | potassium persulfate, 4.0% water, 96.0% |

The reactor system was programmed using Impressionist™ software (Symyx Technologies, Inc., Santa Clara, Calif.) with the following array of volumes (derived from an experimental design array developed using Library Studio™ library design software (Symyx Technologies, Santa Clara, Calif.)) of each feed to add to each vessel, comprising starting materials for an emulsion polymer with targeted polymer content as a linear gradient from 20% polymer to 48% polymer, with constant ratios of 2.4% surfactant and 0.8% initiator to the amount of monomer, and an aim mass of 6.0 g of total material added to each of the eight vessels. The reactor was further programmed to add the feeds to the reactor with the following feed profile:

| Stage | Start time (s) | End time (s) | Number of portions | Stage Description |
|---|---|---|---|---|
| 1 | 0 | 1 | 1 | Initial reactor charge |
| 2 | 600 | 8400 | 200 | Initiator addition |
| 3 | 720 | 7920 | 200 | Monomer addition |

Feeds 1 and 2 (monomers) were programmed to all be added as a linear 120 minute ramp feed in stage 3, with an allowable number of portions of 200, allowing individual additions as small as 1/200 of the total requested volume, if permitted by hardware and external timing considerations. Feed 3 (water) was added entirely in stage 1. The initial reactor charge components were allowed to stir and heat for 10 minutes before addition of monomer or surfactant. Feed 4 (surfactant) was added 25% in stage 1 and 75% in stage 3). Feed 5 (initiator) was added in stage 2, in a 130 minute ramp similar to stage 3, but beginning two minutes earlier and ending eight minutes later. The temperature of the reactor was controlled at 80° C. at the beginning of the reaction, with heating stopped to allow cooling to room temperature at 3.0 hours (10,800 seconds). The stirring rate was set to 900 rpm. The reactions were allowed to cool to <50° C. before the stirring was stopped, the reactor opened, and the reaction products isolated.

| Feed#/Vessel | 1, 20% | 2, 24% | 3, 28% | 4, 32% | 5, 36% | 6, 40% | 7, 44% | 8, 48% |
|---|---|---|---|---|---|---|---|---|
| 1, μL | 1336.3 | 1603.6 | 1870.8 | 2138.1 | 2405.3 | 2672.6 | 2939.9 | 3207.1 |
| 2, μL | 0 | 0 | 0 | 0 | 0 | 0 | 0 | 0 |
| 3, μL | 4328.3 | 3978.1 | 3628.0 | 3277.8 | 2927.7 | 2577.5 | 2227.4 | 1877.2 |
| 4, μL | 291.8 | 350.2 | 408.5 | 466.9 | 525.2 | 583.6 | 641.9 | 700.3 |
| 5, μL | 243.2 | 291.8 | 340.4 | 389.1 | 437.7 | 486.3 | 535.0 | 583.6 |

(feed line designation number, mass % monomer)

(reaction vessel designation number, volume)

Well-behaved, relatively low-viscosity emulsions were obtained, with little or no apparent skinning, drying, or coagulum formation. Average particle sizes of the emulsions were determined by dynamic light scattering, and percent solids measurements were obtained by microwave drying of weighed samples, as shown below, demonstrating excellent emulsion quality and good agreement of theoretical measured solids content for the emulsions.

| Feed/Vessel | 1 | 2 | 3 | 4 | 5 | 6 | 7 | 8 |
|---|---|---|---|---|---|---|---|---|
| Particle radius, DLS, nm | 32 | 32 | 35 | 31 | 32 | 40 | 37 | 42 |
| % solids, theory | 20.6 | 24.8 | 28.9 | 33.0 | 37.2 | 41.3 | 45.4 | 49.5 |
| % solids, measured | 20.7 | 25.2 | 29.0 | 32.6 | 37.6 | 41.4 | 44.7 | 49.2 |

In a similar manner, eight emulsion polymer samples utilizing all five feeds were prepared, adding styrene in place of 25% of the monomer mix, as in the following table.

| Feed#/Vessel* | 1, 20% | 2, 24% | 3, 28% | 4, 32% | 5, 36% | 6, 40% | 7, 44% | 8, 48% |
|---|---|---|---|---|---|---|---|---|
| 1, μL | 1002.2 | 1202.7 | 1403.1 | 1603.6 | 1804.0 | 2004.5 | 2204.9 | 2405.3 |
| 2, μL | 330.0 | 396.0 | 462.0 | 528.1 | 594.1 | 660.1 | 726.1 | 792.1 |
| 3, μL | 4328.3 | 3978.1 | 3628.0 | 3277.8 | 2927.7 | 2577.5 | 2227.4 | 1877.2 |
| 4, μL | 291.8 | 350.2 | 408.5 | 466.9 | 525.2 | 583.6 | 641.9 | 700.3 |
| 5, μL | 243.2 | 291.8 | 340.4 | 389.1 | 437.7 | 486.3 | 535.0 | 583.6 |

(feed line designation number, mass % monomer)
(reaction vessel designation number, volume)

The experiment was run in a manner substantially as described above.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A parallel, semi-continuous or continuous, pressure reactor comprising
    a reactor block comprising four or more semi-continuous or continuous reaction vessels for containing liquid reaction mixtures, each of the four or more reaction vessels being pressurizable to a pressure of not less than about 50 psig,
    four or more shaft-driven impellers corresponding to the four or more reaction vessels for stirring the reaction mixtures, and
    at least four liquid feed lines in selectable fluid communication with each of the four or more reaction vessels, each of the at least four liquid feed lines being in fluid communication with one or more liquid reagent source vessels, such that one or more liquid reagents can be selectively fed from the one or more source vessels to each of the four or more reaction vessels during a reaction under reaction conditions.

2. A parallel, semi-continuous or continuous, pressure reactor comprising
    four or more semi-continuous or continuous reaction vessels for containing liquid reaction mixtures, each of the four or more reaction vessels having a volume of not more than about 1 liter, and being pressurizable to a pressure of not less than about 50 psig,
    four or more shaft-driven impellers corresponding to the four or more reaction vessels for stirring the reaction mixtures, and
    at least four liquid feed lines in selectable fluid communication with each of the four or more reaction vessels, each of the at least four liquid feed lines being in fluid communication with one or more liquid reagent source vessels, such that one or more liquid reagents can be selectively fed from the one or more source vessels to each of the four or more reaction vessels during a reaction under reaction conditions.

3. A parallel, semi-continuous or continuous, pressure reactor comprising
    four or more semi-continuous or continuous reaction vessels for containing liquid reaction mixtures, each of the four or more reaction vessels being pressurizable to a pressure of not less than about 50 psig,
    at least four liquid feed lines in selectable fluid communication with each of the four or more reaction vessels, each of the at least four liquid feed lines being in fluid communication with one or more liquid reagent source vessels, such that one or more liquid reagents can be selectively fed from the one or more source vessels to each of the four or more reaction vessels during a reaction under reaction conditions,
    at least one feed-pressurization station pressurizable to a pressure of not less than about 50 psig, at least a portion of each of the at least four liquid feed lines being in selectable fluid communication with the at least one feed-pressurization station, such that said portion of each of the at least four liquid feed lines can be selectively pressurized prior to feeding the one or more liquid reagents to the four or more reaction vessels.

4. The parallel reactor of claim 3 wherein the feed-pressurization station comprises a waste vessel.

5. The parallel reactor of claims 1 or 2 further comprising at least one feed-pressurization station pressurizable to a pressure of not less than about 50 psig, each of the at least four liquid feed lines being in selectable fluid communication with the at least one feed-pressurization station, such that each of said at least four liquid feed lines can be selectively pressurized prior to feeding the one or more liquid reagents to the four or more reaction vessels.

6. The parallel reactor of claim 5 wherein the feed-pressurization station comprises a waste vessel.

7. The parallel reactor of claims 2 or 3 further comprising a reactor block comprising the four or more semi-continuous or continuous reaction vessels.

8. The parallel reactor of claim 3 further comprising four or more shaft-driven impellers corresponding to the four or more reaction vessels for stirring the reaction mixtures.

9. The parallel reactor of claims 3 or 8 wherein each of the four or more reaction vessels has a volume of not more than about 1 liter.

10. The parallel reactor of claim 9 further comprising a reactor block comprising the four or more semi-continuous or continuous reaction vessels.

11. The parallel reactor of claim 1 wherein the at least four liquid feed lines are provided to each of the four more reaction vessels through one or more modular feed-line subassemblies, each of the feed-line subassemblies being adapted to releasably engage the reactor block and to support at least two of said liquid feed lines passing into a respective reaction vessel.

12. The parallel reactor of claim 11 wherein the one or more modular feed-line subassemblies comprises a ferrule comprising two or more apertures adapted to sealingly support the at least two liquid feed lines when the ferrule is engaged with the reactor block.

13. The parallel reactor of claim 1 wherein the at least four liquid feed lines comprise capillaries having an inside diameter of not more than about 1 mm.

14. The parallel reactor of claim 1 wherein the at least four liquid feed lines comprise capillaries having an outside diameter of not more than about 1 mm.

15. The parallel reactor of claim 1 wherein the at least four liquid feed lines comprise fused silica capillaries.

16. The parallel reactor of claim 1 wherein the at least four liquid feed lines comprise stainless steel capillaries.

17. The parallel reactor of claim 1 wherein the at least four liquid feed lines comprise polymer capillaries.

18. The parallel reactor of claim 1 wherein each of the four or more reaction vessels is defined by or contained in a lower portion of a reaction cavity in the reactor block, the reaction cavity being further defined by an upper portion in the reactor block, the upper portion of the reaction cavity having a larger cross section, taken radially, relative to the lower portion, and the reaction cavity being sized such that two or more of the at least four liquid feed lines can be passed through the upper portion to the lower portion of the reaction cavity.

19. The parallel reactor of claim 1 wherein each of the four or more reaction vessels is defined by or contained in a reaction cavity in the reactor block, the reaction cavity having a substantially uniform cross section, taken radially.

20. The parallel reactor of claim 19 wherein the reaction cavity comprises a cylindrical reaction cavity.

21. The parallel reactor of claim 1 wherein each of the at least four liquid feed lines in fluid communication with each of the four or more reaction vessels comprises at least a first section and a second section in fluid communication with each other, the second section being releasable with respect to the first section and having a distal end positioned within the reaction vessel.

22. The parallel reactor of claim 21 wherein the first section is positioned such that it is outside of the reaction vessel, and additionally or alternatively, at least substantially uncontaminated by the liquid reaction mixture.

23. The parallel reactor of claim 21 wherein the first section is positioned such that at least a portion thereof is inside a reaction cavity that contains or defines the reaction vessel.

24. The parallel reactor of claim 1 wherein each of the least four liquid feed lines has a distal end positioned within the reaction vessel, the distal end of one or more of the liquid feed lines being positioned lower in the reaction vessel relative to the distal end of one or more other of the liquid feed lines.

25. The parallel reactor of claim 24 wherein the distal end of one or more of the liquid feed lines is positioned in the reaction vessel such that feed is delivered through such one or more liquid feed lines directly into the liquid reaction mixture, and the distal end of one or more other of the liquid feed lines is positioned in the reaction vessel such that feed is delivered through such one or more other liquid feed lines into a gaseous headspace above the liquid reaction mixture.

26. The parallel reactor of claim 1 wherein the inside diameter or cross-sectional flow area of one or more of the at least four liquid feed lines is different from the inside diameter or cross-sectional flow area for another of the at least four liquid feed lines.

27. The parallel reactor of claim 1 wherein each of the at least four liquid feed lines has a substantially circular cross-sectional area, the inside diameter of one or more of the liquid feed lines is less than about 500 $\mu$m, and the inside diameter for another of the liquid feed lines is about 500 $\mu$m or more.

28. The parallel reactor of claim 1 further comprising a parallel feed-line interface providing fluid communication between a first section and a second section of each of at least four liquid feed lines, the interface being releasable with respect to the first section and additionally or alternatively, to the second section, of each of the at least four liquid feed lines.

29. The parallel reactor of claim 1 wherein at least one liquid feed line for each of the four or more reaction vessels is in direct fluid communication with a liquid reagent source vessel.

30. The parallel reactor of claim 1 further comprising at least one feed distribution valve providing selective fluid communication between one or more liquid reagent source vessels and at least one liquid feed line for each of the four or more reaction vessels.

31. The parallel reactor of claim 1 further comprising at least one syringe-type feed pump for feeding one or more liquid reagents from one or more source vessels through one or more of the liquid feed lines to the selected one or more reaction vessels.

32. The parallel reactor of claim 1 wherein the four or more reaction vessels comprise semi-continuous flow reaction vessels.

33. The parallel reactor of claim 1 wherein the four or more reaction vessels comprise continuous-flow reaction vessels.

34. The parallel reactor of claim 1 further comprising four or more gas ports, each of the four or more gas ports providing fluid communication to a respective one of the four or more reaction vessels.

35. The parallel reactor of claim 1 further comprising four or more pairs of gas ports, each of the pairs of gas ports providing fluid communication with a respective one of the four or more reaction vessels.

36. The parallel reactor of claim 34 wherein each of the four or more gas ports comprises a gaseous feed port, a pressure monitoring port, a pressure control port, or a gaseous purge port.

37. The parallel reactor of claim 1 further comprising four or more discharge lines, each of the four or more discharge lines providing fluid communication to a respective one of the four or more reaction vessels.

38. The parallel reactor of claim 1 wherein the four or more reaction vessels comprise wells formed in the reactor block.

39. The parallel reactor of claim 1 wherein the four or more reaction vessels comprise removable liners supported by wells formed in the reactor block, each of the liners having an interior surface defining a cavity for containing a respective one of the liquid reaction mixtures, and an external surface dimensioned to fit within the wells.

40. The parallel reactor of claim 39 wherein the removable liners comprise glass vials.

41. The parallel reactor of claim 1 wherein each of the four or more reaction vessels has an aspect ratio (L/D) of at least about 1.5.

42. The parallel reactor of claim 1 wherein each of the four or more reaction vessels has an aspect ratio (L/D) of at least about 2.

43. The parallel reactor of claim 1 wherein the reactor block comprises a base block comprising four or more wells defining or containing the four or more reaction vessels, and a header block positioned over the base block to form four or more pressurizable reaction cavities, each of the four or more reaction cavities defining or containing a respective one of the four or more reaction vessels.

44. The parallel reactor of claim 43 wherein the header block supports the four or more shaft-driven impellers.

45. The parallel reactor of claim 44 further comprising a disposable header gasket situated between the base block and the header block, the disposable header gasket including four or more masking regions corresponding to the four or more reaction cavities, each of the four or more masking regions being adapted to mask a portion of the header block exposed to a respective reaction cavity.

46. The parallel reactor of claims 1, 44 or 45 further comprising four or more disposable shaft covers corresponding to the four or more shaft-driven impellers, each of the four or more shaft covers being adapted to mask at least a non-disposable portion of a shaft of a respective shaft-driven impeller received in a respective reaction cavity.

47. The parallel reactor of claim 11 wherein the reactor block comprises a base block comprising four or more wells defining or containing the four or more reaction vessels, and a header block positioned over the base block to form four or more pressurizable reaction cavities, each of the four or more reaction cavities defining or containing a respective one of the four or more reaction vessels, the header block further comprising four or more feed-line subassembly receiving ports adapted to receive respective modular feed-line subassemblies.

48. The parallel reactor of claim 1 wherein each of the four or more reaction vessels has a volume of not more than about 500 ml.

49. The parallel reactor of claim 1 wherein each of the four or more reaction vessels has a volume ranging from about 1 ml to about 100 ml.

50. The parallel reactor of claim 1 wherein each of the four or more reaction vessels is pressurizable to a pressure of not less than about 400 psig.

51. The parallel reactor of claim 1 wherein each of the four or more reaction vessels is pressurizable to a pressure ranging from about 500 psig to about 1500 psig.

52. The parallel reactor of claim 1 wherein the reactor block further comprises one or more temperature control elements for individual or modular temperature control of the four or more reaction vessels.

53. A parallel, semi-continuous or continuous, pressure reactor comprising
a reactor block comprising a base block and a header block, the base block comprising eight or more wells, each of the eight or more wells containing a removable reaction vessel for containing a liquid reaction mixture, the reaction vessels having a volume of not more than about 1 liter, the header block being removably positioned over the base block for access to the reaction vessels and for forming eight or more pressurizable reaction cavities that include the eight or more wells containing the reaction vessels, the reaction cavities being pressurizable to a pressure of not less than about 100 psig,
eight or more shaft-driven impellers corresponding to the eight or more reaction vessels for stirring the reaction mixtures, the eight or more shaft-driven impellers being supported by the header block,
at least four liquid feed lines in selectable fluid communication with each of the eight or more reaction vessels, each of the at least four liquid feed lines being in fluid communication with one or more liquid reagent source vessels, and
eight or more modular feed-line subassemblies releasably received in receiving ports in the header block, each of the eight or more feed-line subassemblies being adapted to sealingly support the at least four liquid feed lines feeding a respective reaction vessel.

54. The parallel reactor of claim 53 wherein the reactor block comprises a first modular reactor block, the parallel reactor comprising one or more additional modular reactor blocks, each of the one or more additional modular reactor blocks comprising
a base block and a header block, the base block comprising eight or more wells, each of the eight or more wells containing a removable reaction vessel for containing a liquid reaction mixture, the reaction vessels having a volume of not more than about 1 liter, the header block being removably positioned over the base block for access to the reaction vessels and for forming eight or more pressurizable reaction cavities that include the eight or more wells containing the reaction vessels, the reaction cavities being pressurizable to a pressure of not less than about 100 psig, and corresponding thereto,
eight or more shaft-driven impellers corresponding to the eight or more reaction vessels for stirring the reaction mixtures, the eight or more shaft-driven impellers being supported by the header block,
at least four liquid feed lines in selectable fluid communication with each of the eight or more reaction vessels, each of the at least four liquid feed lines being in fluid communication with one or more liquid reagent source vessels, and
eight or more modular feed-line subassemblies releasably received in receiving ports in the header block, each of the eight or more feed-line subassemblies being adapted to sealingly support the at least four liquid feed lines feeding a respective reaction vessel.

55. A parallel, semi-continuous or continuous reactor comprising four or more semi-continuous or continuous reaction vessels for containing liquid reaction mixtures, each of the four or more reaction vessels is hermetically sealable and has volume of not more than about 1 liter, at least four liquid feed lines in selectable fluid communication with each of the four or more reaction vessels, each of the at least four liquid feed lines being in fluid communication with one or more liquid reagent source vessels, four or more modular feed-line subassemblies releasably received in receiving ports in the reaction vessels or in a reactor block that defines or contains the reaction vessels, each of the four or more feed-line subassemblies supporting two or more of the at least four liquid feed lines feeding a respective reaction vessel.

56. A parallel, semi-continuous or continuous reactor comprising four or more semi-continuous or continuous reaction vessels for containing liquid reaction mixtures, each of the four or more reaction vessels is hermetically sealable and has a volume of not more than about 1 liter, at least four liquid feed lines in selectable fluid communication with each of the four or more reaction vessels, each of the at least four liquid feed lines being in fluid communication with one or more liquid reagent source vessels, each of the at least four liquid feed lines comprising at least a first section and a second section in fluid communication with each other, the second section being releasable with respect to the first section and having a distal end positioned within a respective one of the reaction vessels.

57. A parallel, semi-continuous or continuous reactor comprising four or more semi-continuous or continuous reaction vessels for containing liquid reaction mixtures, each of the four or more reaction vessels is hermetically sealable and has a volume of not more than about 1 liter, at least four liquid feed lines in selectable fluid communication with each of the four or more reaction vessels, each of the at least four liquid feed lines being in fluid communication with one or more liquid reagent source vessels, each of the at least four liquid feed lines having a distal end positioned within the reaction vessel, the distal end of one or more of the liquid feed lines being positioned lower in the reaction vessel relative to the distal end of one or more other of the liquid feed lines.

58. A parallel, semi-continuous or continuous reactor comprising four or more semi-continuous or continuous reaction vessels for containing liquid reaction mixtures, each of the four or more reaction vessels is hermetically sealable and has a volume of not more than about 1 liter, at least four liquid feed lines in selectable fluid communication with each of the four or more reaction vessels, each of the at least four liquid feed lines being in fluid communication with one or more liquid reagent source vessels, one or more of the at least four liquid feed lines having an inside diameter or cross-sectional flow area that differs from the inside diameter or cross-sectional flow area for another of the at least four liquid feed lines.

59. The parallel reactor of claims 55, 56, 57 or 58 further comprising four or more shaft-driven impellers corresponding to the four or more reaction vessels for stirring the reaction mixtures.

60. The reactor of claims 55, 56, 57 or 58 wherein the four or more reaction vessels comprise semi-continuous flow reaction vessels.

61. The parallel reactor of claims 55, 56, 57 or 58 wherein the four or more reaction vessels comprise continuous flow reaction vessels.

62. The parallel reactor of claim 55, 56, 57 or 58 wherein the four or more reaction vessels comprise removable liners supported by wells formed in a reactor block, each of the liners having an interior surface defining a cavity for containing a respective liquid reaction mixture, and an external surface dimensioned to fit within a respective well.

63. The parallel reactor of claim 55, 56, 57 or 58 wherein the four or more reaction vessels are formed in a reactor block, the reactor block further comprising one or more temperature control elements for individual or modular temperature control of the four or more reaction vessels.

64. The parallel reactor of claim 55, 56, 57 or 58 wherein each of the four or more reaction vessels is pressurizable to a pressure of not less than about 50 psig.

65. A parallel, semi-continuous or continuous, pressure reactor comprising a reactor block comprising four or more semi-continuous or continuous reaction vessels for containing liquid reaction mixtures, each of the four or more reaction vessels being pressurizable to a pressure of not less than about 50 psig, four or more shaft-driven impellers corresponding to the four or more reaction vessels for stirring the reaction mixtures, and at least four liquid feed lines in selectable fluid communication with each of the four or more reaction vessels, each of the at least four liquid feed lines being in fluid communication with one or more liquid reagent source vessels, such that one or more liquid reagents can be selectively fed from the one or more source vessels to each of the four or more reaction vessels during a reaction under reaction conditions, wherein the at least four liquid feed lines are provided to each of the four more reaction vessels through one or more ferrules, the reactor block further comprising four or more receiving ports adapted to receive a respective one of the ferrules, each of the receiving ports being in fluid communication with a respective one of the reaction vessels, each of the one or more ferrules comprises a first interior end for insertion into the corresponding receiving port in the reactor block, a second exterior end substantially opposing the first interior end, four or more internal apertures extending from the first interior end to the second exterior end for supporting the at least four liquid feed lines passing into a respective one of the reaction vessels, the four or more internal apertures of the ferrule being adapted to sealingly support the at least four liquid feed lines when the ferrule is engaged with the receiving port, an external side surface including a tapered portion, the tapered portion having a smaller cross-section at positions closer to the first interior end relative to positions farther from the first interior end, the tapered portion being configured to correspond to a tapered surface defining a portion of the receiving port, and a fastener for releasably engaging at least the tapered portion of the ferrule with the corresponding tapered surface of the receiving port.

66. A parallel, semi-continuous or continuous, pressure reactor comprising a reactor block comprising four or more semi-continuous or continuous reaction vessels for containing liquid reaction mixtures, each of the four or more reaction vessels being pressurizable to a pressure of not less than about 50 psig, four or more shaft-driven impellers corresponding to the four or more reaction vessels for stirring the reaction mixtures, and at least four liquid feed lines in selectable fluid communication with each of the four or more reaction vessels, each of the at least four liquid feed lines being in fluid communication with one or more liquid reagent source vessels, such that one or more liquid reagents can be selectively fed from the one or more source vessels to each of the four or more reaction vessels during a reaction under reaction conditions, wherein each of the four or more reaction vessels is defined by or contained in a lower portion of a reaction cavity in the reactor block, wherein the lower portion of the reaction cavity has a substantially circular cross section, taken radially, the reaction cavity being further defined by an upper portion in the reactor block, wherein the upper portion of the reaction cavity has a substantially oval cross section, taken radially, the upper portion of the reaction cavity having a larger cross section, taken radially, relative to the lower portion, and the reaction cavity being sized such that two or more of the at least four liquid feed lines can be passed through the upper portion to the lower portion of the reaction cavity.

67. A parallel, semi-continuous or continuous, pressure reactor comprising a reactor block comprising four or more semi-continuous or continuous reaction vessels for containing liquid reaction mixtures, each of the four or more reaction vessels being pressurizable to a pressure of not less than about 50 psig, four or more shaft-driven impellers corresponding to the four or more reaction vessels for stirring the reaction mixtures, and at least four liquid feed lines in selectable fluid communication with each of the four or more reaction vessels, each of the at least four liquid feed lines being in fluid communication with one or more liquid reagent source vessels, such that one or more liquid reagents can be selectively fed from the one or more source vessels to each of the four or more reaction vessels during a reaction under reaction conditions, wherein each of the least four liquid feed lines in fluid communication with each of the four or more reaction vessels comprises at least a first section and a second section in fluid communication with each other, the second section being releasable with respect to the first section and having a distal end positioned within the reaction vessel, and wherein the first section comprises a polymer capillary and the second section comprises a stainless steel capillary.

* * * * *